(12) United States Patent
Laeseke et al.

(10) Patent No.: US 11,207,171 B2
(45) Date of Patent: Dec. 28, 2021

(54) CATHETER APPARATUS AND METHOD

(71) Applicant: Wisconsin Alumni Research Foundation, Madison, WI (US)

(72) Inventors: Paul Laeseke, Madison, WI (US); Michael Woods, Madison, WI (US); Emily Rae Foran, Madison, WI (US); Will Robert Flanigan, Madison, WI (US); Alexandra Nicol Doersch, Madison, WI (US); Brett Conor Struthers, Madison, WI (US); Joseph Alexander Ashley, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 294 days.

(21) Appl. No.: 16/397,621

(22) Filed: Apr. 29, 2019

(65) Prior Publication Data

US 2020/0222168 A1 Jul. 16, 2020

Related U.S. Application Data

(60) Provisional application No. 62/663,990, filed on Apr. 27, 2018.

(51) Int. Cl.
*A61F 2/01* (2006.01)
*A61M 25/00* (2006.01)
*A61B 17/00* (2006.01)
*A61M 25/09* (2006.01)

(52) U.S. Cl.
CPC ...... *A61F 2/01* (2013.01); *A61B 2017/00292* (2013.01); *A61F 2/011* (2020.05); *A61M 25/0082* (2013.01); *A61M 25/09* (2013.01)

(58) Field of Classification Search
CPC .......... A61F 2/01; A61F 2/0105; A61F 2/011; A61F 2210/009; A61B 2017/00292; A61M 25/0082; A61M 25/0127; A61M 2025/0163; A61M 25/09
See application file for complete search history.

(56) References Cited

U.S. PATENT DOCUMENTS

2005/0228422 A1* 10/2005 Machold .......... A61B 17/00234
606/167
2008/0091264 A1* 4/2008 Machold ............... A61F 2/2487
623/2.1

OTHER PUBLICATIONS

"Peripheral Intraveous Catheters (PIVC)." Smiths Medical, https://www.smithsmedical.com/products/peripheral-iv-catheters [Accessed Dec. 3, 2017].

(Continued)

*Primary Examiner* — George J Ulsh
(74) *Attorney, Agent, or Firm* — Crawford Maunu PLLC

(57) ABSTRACT

Aspects of the disclosure are directed to methods and/or apparatuses involving the deployment and coupling of catheters. As may be implemented in accordance with one or more embodiments, each of first and second catheters extend from a proximal end to a distal end and has a magnet. The catheters may be deployed, and the distal ends of the respective catheters can be aligned and connected via magnetic coupling of the magnets to one another. A shaft structure is configured and arranged to extend within the first catheter and into the second catheter, through the connected distal ends of the respective catheters.

22 Claims, 27 Drawing Sheets

(56) References Cited

OTHER PUBLICATIONS

"Inferior Vena Cava Filter Placement and Removal." Radiologyinfo. Jun. 21, 2016. Available: https://www.radiologyinfo.org/en/pdf/VenaCavaFilter.pdf [Accessed Oct. 3, 2017].
American Heart Association Available: http://www.heart.org/HEARTORG/Conditions/More/Whatis-Venous-Thromboembolism-VTE_UCM_479052_Article.jsp#.WcR5Za2-KqA [Accessed: Sep. 12, 2017].
Angel et al., "Systematic review of the use of retrievable inferior vena cava filters," J Vasc Interv Radiol; 22: 1522-1530 (2011).
Becher et al., "Late erosion of a prophylactic Celect IVC filter into the aorta, right renal artery, and duodenal wall," Journal of Vascular Surgery; 52(3):1041-1044 (2010).
Bronzino, "The Biomedical Engineering Handbook, 3rd Ed," Boca Raton, Fla.: CRC Press, pp. 1-5 (2006).
De Gregorio et al., "Retrieval of Gunther Tulip optional vena cava filters 30 days after implantation: a prospective clinical study," J Vascular Interventional Radiology, 17(11): 1781-9 (Nov. 2006).
Dillavou, "The ABCs of IVC Filters: IVC Filters Data, Types, Techniques and Retrievals." Vein Magazine. Available: https://www.veindirectory.org/magazine/article/techniques-technology/theabcs-of-ivc-filters-ivc-filters-data-types-techniques-and-retrieval. [Accessed Oct. 8, 2017].
Doe et al., "Anatomic and Technical Considerations: Inferior Vena Cava Filter Placement." Seminars in Interventional Radiology; 33(2):88-92 (Jun. 2016).
Fedullo et al., "Placement of vena cava filters and their complications." UpToDate. Sep. 2017. Available: https://www-uptodate-com.ezproxy.library.wisc.edu/contents/placement-of-vena-cava-filters-and-theircomplications?source=search_result&search=Placement%20of%20vena%20cava%20filters%20and%20their%20complications&selectedTitle=1~150 [Accessed Sep. 29, 2017].
Fornell, "The Basics of Guide Wire Technology." Diagnostic and interventional Radiology; Mar. 18, 2011.; https://www.dicardiology.com/article/basics-guide-wire-technology [Accessed Oct. 3, 2017].
Fronek, "Common femoral vein dimensions and hemodynamics including Valsalva response as a function of sex, age, and ethnicity in a population study," Journal of Vascular Surgery; 33(5):1050-1056 (May 2001).
Gaspard et al., "Retreivable Inferior vena cava filters are rarely removed," Am Surg.; 75:426-428 (2009).
Ge et al., "Central venous access sites for the prevention of venous thrombosis, stenosis and infection," Cochrane Database of Systematic Reviews 2012, Issue 3. Art. No. CD004084. DOI: 10.1002/14651858.CD004084.pub3.
Gyang et al., (2013). Factors impacting followup care after placement of temporary inferior vena cava filters. [Online] Science Direct. Available at: http://www.sciencedirect.com/science/article/pii/S0741521413001912 [Accessed Oct. 3, 2017].
Harvey, "Inferior vena cava filters: What radiologists need to know." Department of Diagnostic and Interventional Radiology; 68(7)721-732 (Jul. 2013).
Iliescu et al., "Advanced Techniques for Removal of Retrievable Inferior Vena Cava Filters", CardioVascular and Interventional Radiology; 35(4): 741-750 (2011).
Kim et al., "A comparison of clinical outcomes with retrievable and permanent inferior vena cava filters," Journal of Vascular Interventional Radiology; 19(3):393-399 (2008).
Kuo et al., "Complex Retrieval of Fractured, Embedded, and Penellaling Inferior Vena Cava Filters: A Prospective Study with Histologic and Electron Microscopic Analysis," J Vasc Interv Radiol; 24(5): 622-630 (2013).
Kuo et al., "Laser-Assisted Removal of Embedded Vena Cava Filters", Chest; 151(2):417-424 (2017).
Laws et al., "Retrieval of Inferior Vena Cava Filters: Technical Considerations." Seminars in Interventional Radiology; 33(2):144-148 (Jun. 2016).
Lynch, "A method for following patients with retrievable inferior vena cava filters: results and lessons learned from the first 1,100 patients;" J Vasc Interv Radiol; 1507-1512 (2011).
Martin, "Common Equipment in Interventional Radiology." Springer Link. https://link.springer.com/chapter/10.1007/978-3-319-17238-5_4 [Accessed Dec. 3, 2017].
Mayo Clinic "IVC filter retrieval—Radiology—Mayo Clinic", Mayoclinic.org, 2017. [Online], http://www.mayoclinic.org/departments-centers/radiology/services/ivc-filter-retrieval. [Accessed: Sep. 12, 2017].
Minocha et al., "Improving inferior vena cava filter retrieval rates: impact of a dedicated inferior vena cava filter clinic," J Vasc Interv Radiol; 21:1847-1851 (2010).
Nat'l Spinal Cord Injury Stat Cntr, "Spinal Cord Injury Facts and Figures at a Glance", J. Spinal Cord Med; 36(4):394-395 (Jul. 2013).
M. Fehlings, A. Singh, L. Tetreault, S. Kalsi-Ryan and A. Nouri, "Global prevalence and incidence of traumatic spinal cord injury", Clinical Epidemiology, p. 309, 2014.
Northcutt, "Wires, Catheters, and More: A Primer for Residents and Fellows Entering Interventional Radiology." RadioGraphics. http://media.rsna.org/media/journals/rg/presentations/2015/35.5.Northcutt/index.html [Accessed Dec. 3, 2017].
Nulife, "Foley Balloon Catheter, 2 Way Catheter and 3 Way Catheter," 2017. [Online]. Available: http://www.nulife.co.in/pdfs/foley-balloon-catheter.pdf. [Accessed: Sep. 12, 2017].
Oh et al., "Removal of retrievable inferior vena cava filters with computed tomography findings indicating tenting or penetration of the inferior vena cava wall," Journal of Vascular and Interventional Radiology; 22(1):70-74 (2011).
Ozaki et al., Venous Thromboembolism | Deep Venous Thrombosis—Pulmonary Embolism,) Cleveland Clinic. 2017. [Online], http://www.clevelandclinicmeded.com/medicalpubs/diseasemanagement/cardiology/venousthromboembolism/. [Accessed: Sep. 12, 2017].
Perouansky, "Neurotoxicity of General Anesthetics: Cause for Concern?" J. American Society of Anesthesiologists, Inc.; 111:1365-1371 (Dec. 2009).
Ray, "Outcomes with retrievable inferior vena cava filters: a multicenter study," J Vasc IntervRadiol; 17:1595-1604 (2006).
Robinson et al., "Healthcare Disparities in IVC Filter Retrieval Rates" 2015 [Online], https://kipdf.com/healthcare-disparities-in-ivc-filter-retrieval-rates_5ab026221723dd329c634ca6.html. [Accessed Jan. 2, 2020].
Rolfe et al., (2011). The Fibrotic Response to Implanted Biomaterials: Implications for Tissue Engineering, Regenerative Medicine and Tissue Engineering—Cells and Biomaterials,Prof. Daniel Eberli (Ed.), ISBN: 978-953-307-663-8,InTech, Available from: http://www.intechopen.com/books/regenerative-medicine-and-tissue-engineering-cells-andbiomaterials/the-fibrotic-response-to-implanted-biomaterials-implications-for-tissue-engineering.
Spectranetics, "CVX-300 Excimer Laser System." Spectranetics. 2015. Available: http://www.spectranetics.com/solutions/peripheral-intervention/cvx-300-excimer-laser-system/ [Accessed Sep. 23, 2017].
Tartiere et al., "Estimation of the diameter and cross-sectional area of the internal jugular veins in adult." US National Library of Medicine: National Institutes of Health. 2009; 13(6): 197.
Taylor, "Inferior Vena Cava." InnerBody: Cardiovascular System of the Lower Torso. Available: http://www.innerbody.com/image_dige07/card26.html#full-description. [Accessed Oct. 2, 2017].
Turba et al., "Before You Place That Filter . . . A guide to IVC filter placement and troubleshooting procedural challenges." Endovascular Today: Optimal IVC Filter Use. Feb. 2010. Available: http://evtoday.com/2010/02/before-you-place-that-filter-/ [Accessed Oct. 2, 2017].
USDHHS, "Fluoroscopy." United States Department of Health and Human Services, https://www.fda.gov/RadiationEmittingProducts/RadiationEmittingProductsandProcedures/MedicalImaging/MedicalXRays/ucm115354.html [Accessed Dec. 3, 2017].
USFDA U.S. Food and Drug Adminisliation. Removing retrievable inferior vena cava filters: initial communication. Aug. 9, 2010, http://www.fda.gov/MedicalDevices/Safety/AlertsandNotices.ucm221676.htm. Accessed Oct. 2012. [Accessed: Sep. 12, 2017].
Van Ha et al., "Use of retrievable compared to permanent inferior vena cava filters: a single institution experience," Cardiovascular Interventional Radiology; 31(2):308-315 (2008).

(56) References Cited

OTHER PUBLICATIONS

Weigel, "Controlling Operating Room Temperature and Humidity, and Managing Expectations", Buildingenergy.cx-associates.com, 2017. [Online]. Available https://buildingenergy.cx-associates.com/2014/12/controlling-operating-room-temperature-andhumidity-and-managing-expectations/. [Accessed: Sep. 12, 2017].

Weinburg et al., "Inferior Vena Cava Filters." JACC: Cardiovascular Interventions; 6(6): 539-547 (Jun. 2013).

Wright, "Using Polyurethanes in Medical Applications," Medical Device and Diagnostic Industry; Mar. 1, 2006. Available: https://www.mddionline.com/using-polyurethanes-medical-applications [Accessed—Oct. 2017].

"Inferior vena Cava Ultrasound for Volume Status." Family Practice Notebook: Cardiovascular Medicine Book. Available: http://www.fpnotebook.com/cv/rad/InfrVnCvUltrsndFrVlmSts.htm [Accessed Sep. 29, 2017].

"Pacemaker Safety." K&J magnetics, Inc. Available: https://www.kjmagnetics.com/blog.asp?p=pacemaker-safety [Accessed Oct. 8, 2017].

"Inductance of a Solenoid." HyperPhysics: Electricity and Magnetism. Available: http://hyperphysics.phy-astr.gsu.edu/hbase/elelectric/indsol.html [Accessed Oct. 8, 2017].

"The Magnetic Field of a Permanent Magnet." Vernier Software & Technology. Available: http://www2.vernier.com/sample_labs/PWV-31-COMP-magnetic_field_permanent_magnet.pdf [Accessed Oct. 8, 2017].

"Introducer Sheath: Radifocus Introducer II Standard Kit-Introducer Sheath." Terumo-Europe. http://www.terumo-europe.com/en-emea/peripheral-intervention/access-diagnostic-products/introducersheat [Accessed Dec. 3, 2017].

"Cook Medical Products." Cook Medical, https://www.cookmedical.com/products/ [Accessed Dec. 3, 2017].

"One Snare Endovascular System." Merit Medical, https://www.merit.com/peripheralintervention/intervention/snares-accessories/one-snare-endovascular-snare-system/ [Accessed Dec. 3, 2017].

* cited by examiner

CATHETER APPARATUS AND METHOD

BACKGROUND

Catheters are used for a multitude of applications, which may involve a variety of different components and may carry out various functions to suit each specific application. Medical catheters are utilized for insertion into a patient for a variety of purposes, such as to treat diseases or to perform medical functions. Such applications may involve, for example, insertion into vascular tissue for medical procedures involving the inspection of tissue, manipulation or modification of tissue (e.g., ablation), delivery of medical devices such as stents, and removal of medical devices.

In many catheter applications, the ability to purposefully place and implement catheters can be useful. For instance, accurately controlling the position of a catheter relative to tissue for treatment, medical device placement, or medical device removal can be very useful. However, doing so can also be challenging, particularly with respect to complex anatomy and/or complex medical device applications.

Certain medical applications requiring intra-vascular access for removal of medical devices can present challenges. For instance, accessing and securely removing medical devices may involve a delicate balance of the application of force and related manipulation of the device to be removed, while protecting the patient. Medical devices may fracture upon the application of force, particularly if they become fragile. In many applications, medical devices are engaged with tissue within the patient and can be challenging to remove.

One particular application that may involve the deployment and subsequent removal of a medical device relates to the use of filters within vascular tissue to filter blood flow. Such filters may be utilized for a variety of purposes, such as to capture blood clots in patients who are susceptible to clotting. For instance, venous thromboembolism (VTE), characterized as patient susceptibility to forming blood clots, affects over 500,000 people each year, resulting in over 300,000 deaths annually. When blood clots dislodge from the lower extremities they can travel to the lungs where a pulmonary embolism may occur, potentially resulting in death. Some patients are fitted with an inferior vena cava (IVC) filter. Many of these filters remain in patients longer than the risk of pulmonary embolism persists, which may result in filter fracture, migration, penetration of the caval wall, or caval thrombosis. However, removing such filters can be challenging, and particularly so for those filters that have become embedded along the caval wall.

These and other matters have presented challenges to catheters, for a variety of applications.

SUMMARY

Various example embodiments are directed to catheter-based apparatuses and methods, which may address various challenges including those noted above.

As may be implemented in accordance with one or more embodiments, an apparatus includes a first catheter, a second catheter and a shaft structure. The first catheter extends from a proximal end to a distal end, the distal end having a magnet. The second catheter extends from a proximal end to a distal end, the distal end having a magnet. The second catheter is configured and arranged with the first catheter to align and connect the distal ends of the respective catheters via magnetic coupling of the magnets to one another. The shaft structure is configured and arranged with the first catheter and the second catheter to, with the first catheter aligned to and connected to the second catheter via the magnetic coupling, extend within the first catheter and into the second catheter, through the connected distal ends of the respective catheters. Various embodiments are directed to methods of coupling catheters and extending shaft structures therein, in accordance with the above.

In accordance with another embodiment, a method for removing a filter from vascular tissue is carried out as follows. A first catheter is deployed into the vascular tissue, the first catheter extending from a proximal end to a distal end, the distal end having a J-curve and a magnet axially aligned with the first catheter, with the J-curve extending partially around a structure of the filter. A second catheter is deployed in the vascular tissue, extending from a proximal end to a distal end, the distal end having a magnet axially aligned with the second catheter and having a magnetic pole that is arranged opposite the pole of the magnet of the first catheter. The distal ends of the respective catheters are aligned and connected via magnetic coupling of the magnets to one another, therein forming a continuous channel through the respective catheters in a loop around the structure of the filter. With the first catheter aligned to and connected to the second catheter via the magnetic coupling and extending in the loop, a wire is extended within the first catheter and into the second catheter, through the connected distal ends of the respective catheters, the wire forming a loop around the structure of the filter. The first and second catheters are then retracted along the wire, exposing the wire in the vascular tissue. The filter is then removed by pulling on the wire, using the looped portion thereof to grasp and dislodge the filter from the vascular tissue.

The above discussion/summary is not intended to describe each embodiment or every implementation of the present disclosure. The figures and detailed description that follow also exemplify various embodiments.

BRIEF DESCRIPTION OF FIGURES

Various example embodiments may be more completely understood in consideration of the following detailed description and in connection with the accompanying drawings, in which:

FIGS. 2A-2J show a catheter apparatus (or apparatuses) at various stages of implementation for retrieving a filter, in accordance with one or more embodiments, and in which:

FIG. 2A shows a first catheter;

FIG. 2B shows a the first catheter with a second catheter positioned relatively, prior to connection;

FIG. 2C shows the first catheter magnetically coupled to the second catheter;

FIG. 2D shows a wire partially inserted within the first catheter;

FIG. 2E shows the wire extending through the first catheter and into the second catheter;

FIG. 2F shows the respective catheters after disconnection;

FIG. 2G shows the second catheter having been partially retracted along the wire;

FIG. 2H shows the first catheter having been partially retracted along the wire;

FIG. 2I shows the wire, with both catheters having been retracted from view; and FIG. 2J shows the wire tightened around a filter for extraction thereof;

FIGS. 6A-6F show respective steps in an approach for coupling respective portions of a catheter in an artery or vein in accordance with one or more embodiments, in which:

FIG. 6A shows a catheter inserted in the artery or vein;

FIG. 6B shows a second catheter inserted into the artery or vein;

FIG. 6C shows advancement of a guide wire;

FIG. 6D shows further advancement of the guide wire;

FIG. 6E shows initial retraction of the catheters; and

FIG. 6F shows removal of the catheters from the body;

FIGS. 7A-7F show respective steps in an approach for coupling respective portions of a catheter in a patient's stomach, in accordance with one or more embodiments, in which:

FIG. 7A shows a catheter inserted in the stomach via the patient's mouth;

FIG. 7B shows a second catheter inserted into the stomach via the patients abdominal wall;

FIG. 7C shows advancement of a guide wire;

FIG. 7D shows further advancement of the guide wire;

FIG. 7E shows initial retraction of the catheters; and

FIG. 7F shows removal of the catheters from the body; and

Figures 1A, 1B:
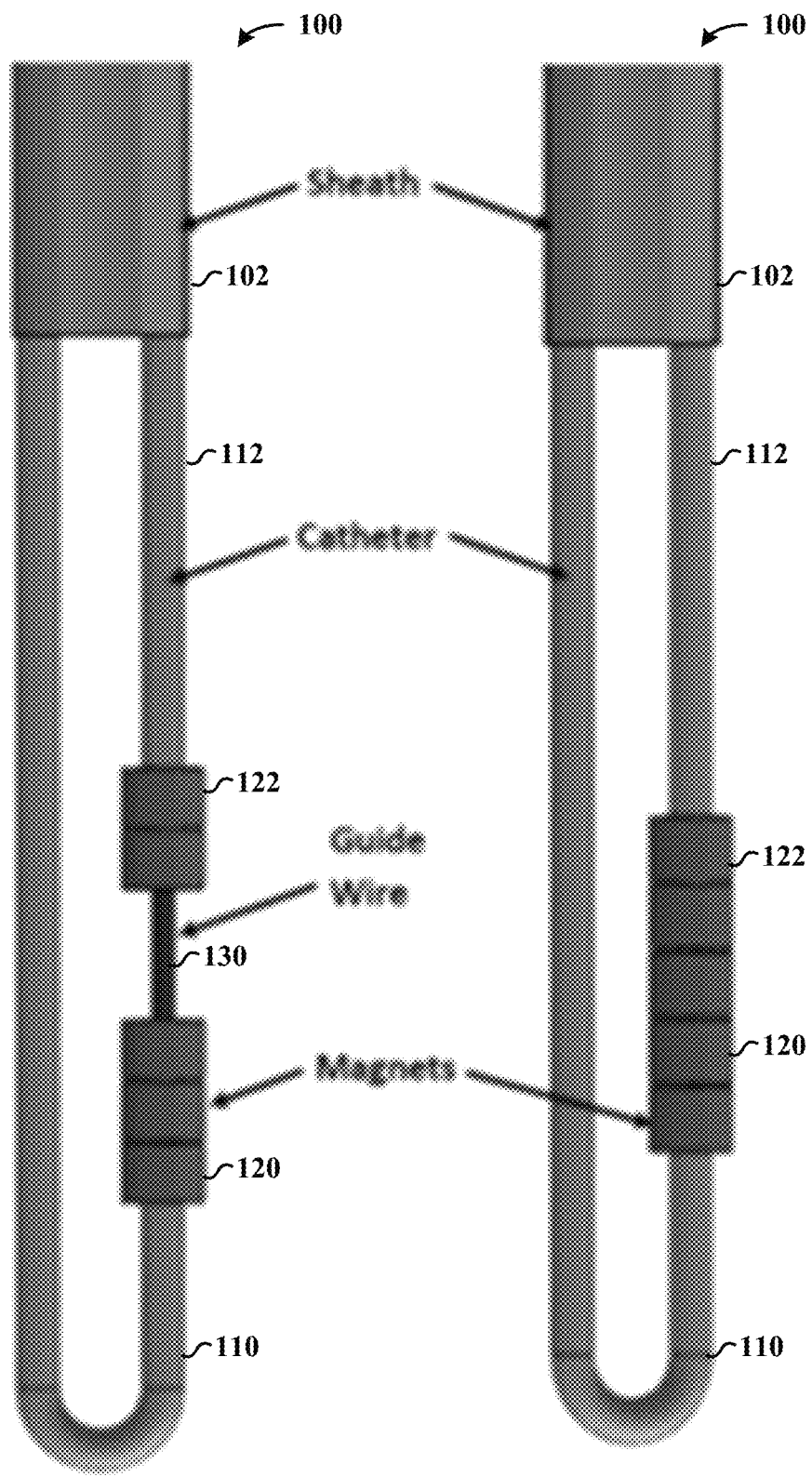
FIGS. 1A and 1B show an apparatus including a "J" type catheter 110 and a straight catheter 112 extending from a sheath 102, in respective states of connectivity, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as may be used throughout this application is by way of illustration, and not limitation.

DETAILED DESCRIPTION

Aspects of the present disclosure are believed to be applicable to a variety of different types of apparatuses, systems and methods involving catheter apparatuses and their implementation. In specific embodiments, two catheters respectively having magnetic ends are operable for joining at the magnetic ends to form a continuous catheter/catheter channel. For instance, each respective catheter can be inserted into vascular tissue and around opposing sides of an object within the vascular tissue, and joined to form a loop around the object. In certain implementations, such an approach further involves a shaft-type structure such as a wire that is passed through the joined catheters. The catheters may subsequently be disconnected and removed, leaving the shaft-type structure in place and looped around the object.

Various aspects of the present disclosure have been shown to be beneficial when used in the context of the removal of objects from vascular tissue (e.g., via the looped wire), such as for IVC filters or other types of filters as noted above. Other applications may involve implementation with chronic total occlusions and feeding tubes. While not necessarily so limited, various aspects may be appreciated through a discussion of examples using such exemplary contexts.

Various aspects of the present disclosure are directed to a catheter apparatus including a "J" type catheter (with a "J" shape) and a second catheter, each catheter having distal ends with magnetic characteristics (e.g., one or more magnets). The respective catheters may be inserted into vascular tissue, joined via the magnetic characteristics/magnets, and therein form a continuous catheter channel through the respective catheters and the joined ends. The "J" type catheter may be positioned such that its "J" shape near its distal end loops around a structure to be removed. The second catheter can be positioned with its magnetic distal end adjacent the magnetic distal and of the "J" type catheter, and joined via magnetic forces. In some instances, the magnetic ends are axially aligned with the respective catheters to facilitate alignment of channels within the catheters and subsequent passage for componentry through the connected distal ends of the respective catheters.

A variety of different types of componentry can be passed through the catheters, once joined. In some embodiments, a wire (e.g., a flexible, 1 mm or less diameter hydrophilic guide wire) is advanced through the magnetically joined catheters to create a snare. Where a "J" type catheter is used, the wire exhibits flexibility, relative to the catheter, such that the wire passes through a "J" bend in the catheter. Once the wire is in place, the catheters can be removed. With a "J" type catheter as noted above, the "straight" catheter can be removed first, utilizing the "J" shape to facilitate disengagement of the magnetic ends. The "J" type catheter can then be retraced along the wire, leaving the wire in place. Such an approach may be utilized to loop one or more wires around an IVC filter, with the wire or wires looped around the filter adapting to small radii of curvature of the IVC filter, and used to remove the IVC filter.

Magnetic attributes can be added to respective catheters as noted herein, in a variety of manners. In some embodiments, magnetic material is integrated within a catheter wall. In other embodiments, magnets are secured to a catheter, such as by shrink wrapping the magnets around an outer wall of the catheter. In still other embodiments, magnetic componentry is inserted at an inner wall of the catheters. Such magnets may be axially aligned to their respective catheters, with opposite poles at the distal ends thereof such that the magnets attract one another along a magnetic field that also aligns the catheters to one another. Accordingly, when the catheters are joined a continuous internal channel may be formed through the respective catheters, which may effectively operate as a single catheter.

In connection with one or more aspects herein, it has been recognized/discovered that, upon insertion of distal ends of catheters having magnetic componentry therein, the magnetic componentry readily aligns the distal ends of the catheters for axial connection. For instance, certain embodiments employ magnets that attract each other at a distance of 27.8+/−1.3 mm away. The resulting connection is strong enough to pass wire through the respective catheters, yet facilitate disconnection by application of tension force along the catheters, for retracing along the wire (therein exposing the wire). Moreover, the utilization of a "J" type catheter and a straight catheter, together with magnetized distal ends, facilitates a highly repeatable and rapid coupling of the catheters around objects to be removed. As the respective catheters are extended within vascular tissue, they tend to follow opposing sidewalls within the vascular tissue and facilitate looping around structures therein. Surprisingly, this approach can be implemented to rapidly deploy a wire snare or snares in a few minute's time, for effectively removing components such as IVC filters, with a very high rate of success for looping around structures.

Various embodiments utilize multiple magnets that may be connected to respective catheters via shrink-wrap or other approaches. There are two catheters: a "J" catheter and a straight catheter, which each serve a specific function. The "J" catheter, with one or more magnets stacked at its tip, is inserted first and allows for directionality to manipulate its position around a device, such as an embedded filter. The straight catheter creates the connection between the two catheters, with one or more magnets at its tip.

The magnets may be secured to the outside of each respective catheter using a 2.5 mm diameter shrink wrap to maintain a smooth path for the wire to travel. Once the magnets are attached, wire (e.g., a 0.89 mm diameter (0.035") wire) is advanced through the catheters to create a snare. When the wire is fed through to the other side, the straight catheter is then removed, followed by the "J" catheter. The flexible wire that remains looped around the device may adapt to small radii of curvature of the device. This in turn allows the magnets to maintain connection while the wire is passed through. The magnetic coupling can facilitate the connection between the two catheters, speeding up the procedure. Additionally, the "J" catheter radius of curvature may be roughly the same size as the IVC, and allows the catheter to more easily bisect the device (e.g., filter) to be removed.

Magnet dissociation can be set to suit particular applications. Forces used when pulling devices, such as pulling filters from the caval wall of vascular tissue, may be about 31.14 N, or 11.12 N and 4.41 N for filter removal. The magnets are chosen to be dissociable with less than average forces, so that the catheters can be safely removed without accidentally dislodging the device simultaneously. For instance, a value of 1.22 N (n=15, SD=0.255) force can be useful to separate the magnetic catheters from each other. This force is significantly less than the minimum 4.41 N force found to be used to remove IVC filters from the caval wall, therefore, the magnets are suitably calibrated to be easily removed without causing the filter to shift before the appropriate time (after the catheters have been removed to expose the guide wire) in such applications.

As may be implemented in accordance with one or more embodiments, an apparatus includes first and second catheters and a shaft structure. The catheters extend from a proximal end to a distal end, with the distal end of each catheter having a magnet that align and connect the magnet at the distal end of the other catheter. One of the catheters may have a "J" type bend, that faces the surface of the distal end back toward the proximal end of the catheters, and which facilitates magnetic coupling with the second catheter. The shaft structure (e.g., a wire) extends within the first catheter and into the second catheter, through the magnetically connected distal ends of the respective catheters. Where the catheters are implemented with a bend, the shaft flexibly extends within the bend as the shaft is extended through the first catheter and into the second catheter via the distal ends of the respective catheters while the distal ends are magnetically connected, therein forming a loop. As such, the stiffness of the shaft can be set such that it will extend through the magnetically connected shafts without breaking the magnetic connection, and stay in place as the catheters are retracted. In some implementations, the apparatus further includes a sheath that houses the catheters, which operate to extend from the sheath with each of the distal ends extending freely and separate from one another, prior to connection of the first catheter to the second catheter.

The catheters may be retracted along the shaft structure in a variety of manners. In some embodiments, the shaft structures are operable to disconnect at the magnets, and retract along the shaft structure that extends from the first catheter into the second catheter through the distal ends of the respective catheters. This retraction exposes the shaft structure for use. The shaft structure may, for example, extend from the proximal end of the first shaft to the proximal end of the second shaft, for use in grasping and removing objects.

The distal ends of the catheters can be implemented in a variety of manners. In some embodiments, the distal end of the first catheter has a surface that mates flush with a surface of the distal end of the second catheter when the respective distal ends are magnetically coupled to one another. The surfaces may be flat, jagged or curved, and fit flush to one another in this regard. The magnets may be axially aligned with poles relative to the respective distal ends, such that they magnetically couple to one another with respective surfaces of the distal ends of the catheters in contact with one another and with the magnets axially aligned to one another. The poles of the magnets on each catheter are thus opposing such that they attract.

Turning now to the figures, FIGS. 1A and 1B show an apparatus 100 including a "J" type catheter 110 and a straight catheter 112 extending from a sheath 102, in respective states of connectivity. Each catheter has magnets 120 and 122 at distal ends thereof, which are configured and arranged to axially align to one another upon connection. In FIG. 1A, the "J" type catheter 110 is shown coupled to the straight catheter 112, via magnets 120 and 122. Such coupling may be carried out as characterized herein, such as to loop the end of the "J" type catheter 110 around an object to be grasped, and subsequently connecting the catheters at their respective distal ends via the magnets. In FIG. 1B, a guide wire 130 is shown having been passed through the aligned catheters (e.g., as in FIG. 1A), and the distal ends have been initially disconnected, with each catheter having been partially withdrawn along the guide wire. Once the "J" type catheter 110 is retracted around the loop end and exposing the portion of the guide wire 130 therein, the guide wire can be utilized for grasping an object, such as to remove a filter as characterized herein.

Figure 2A:
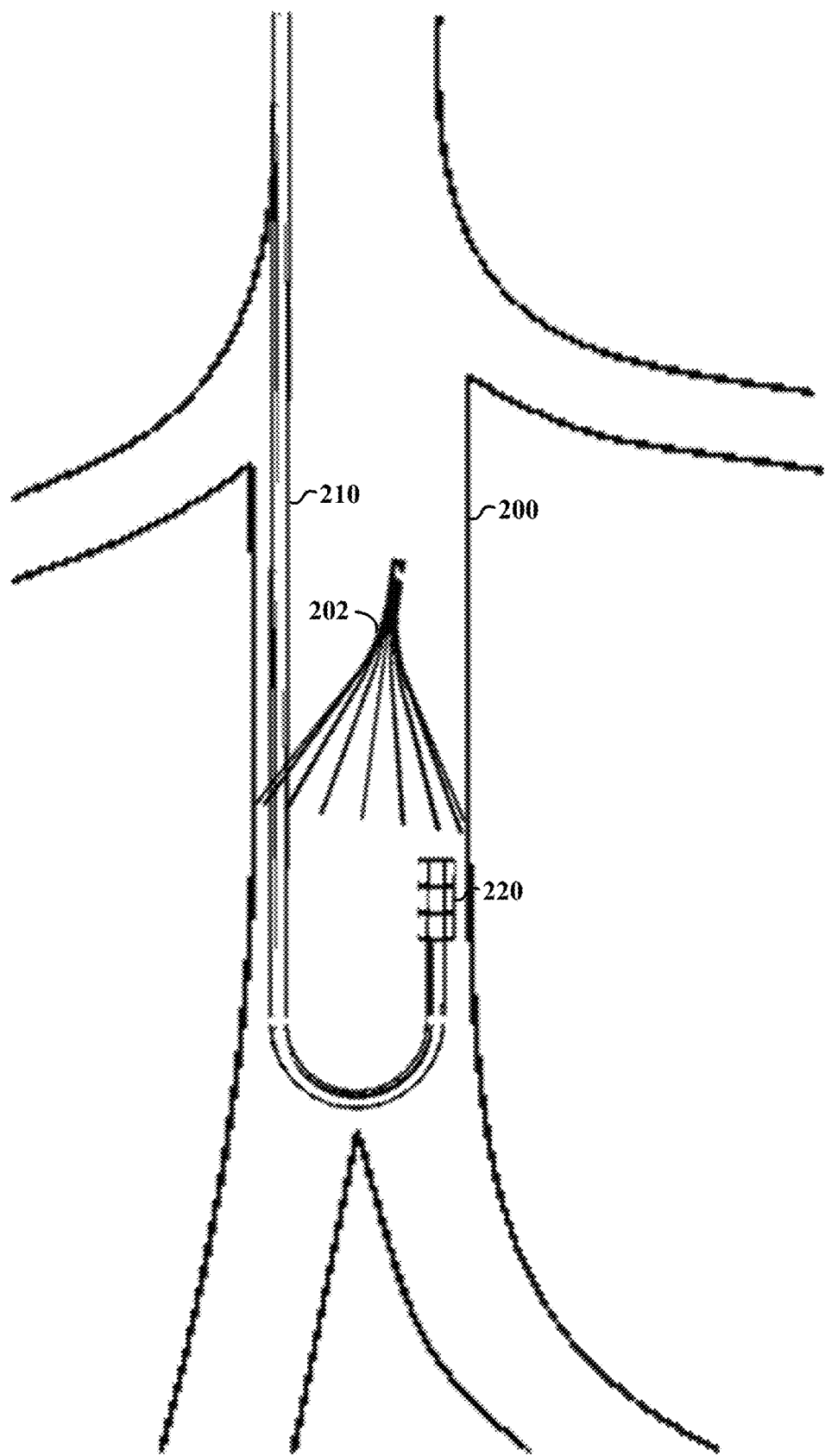
Figure 2B:
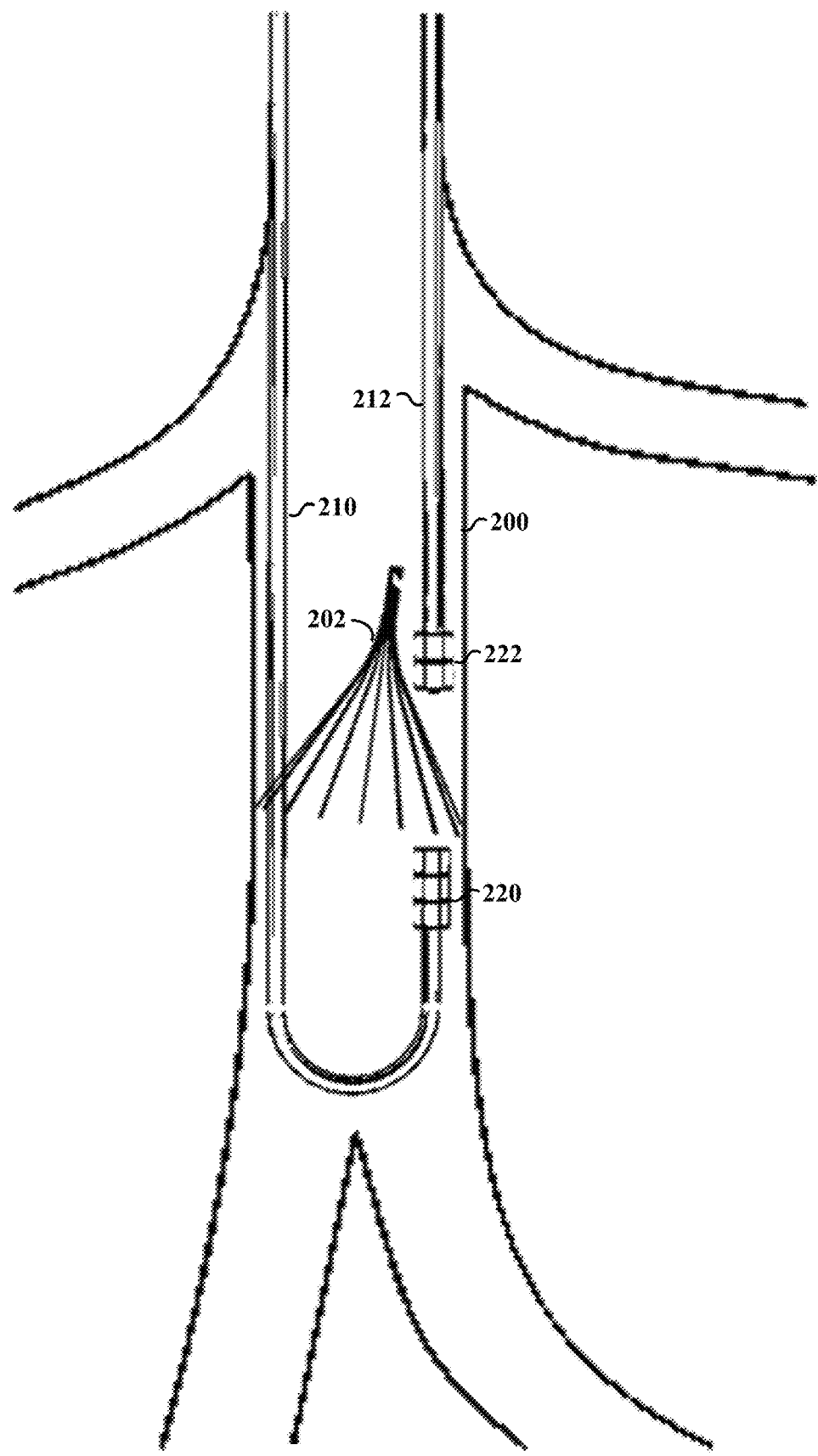
Figure 2C:
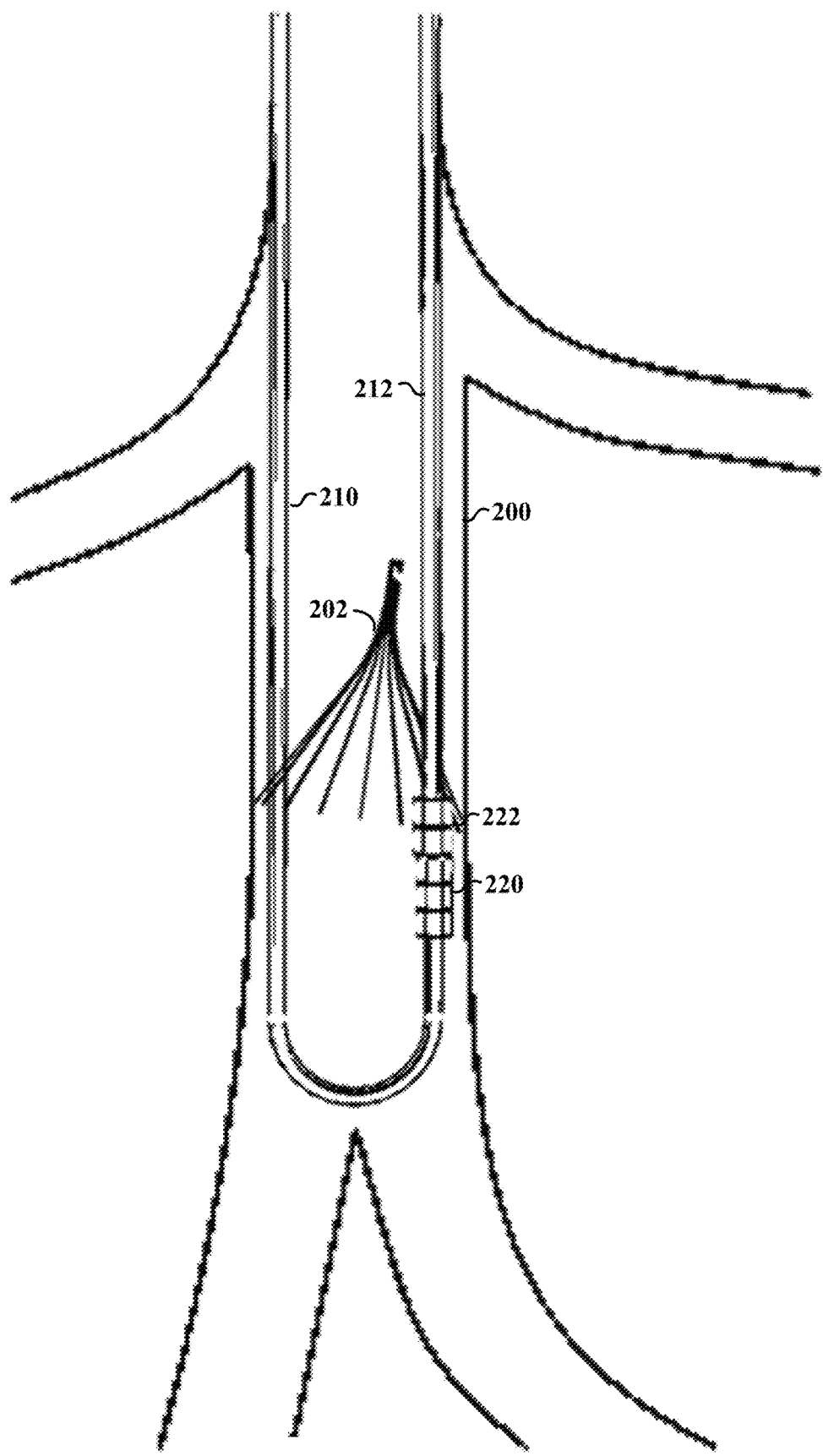

FIGS. 2A-2J show a catheter apparatus (or apparatuses) at various stages of implementation for retrieving a filter 202. Referring to FIG. 2A, a first catheter 210 having a magnetic distal end 220 is shown inserted into vascular tissue 200, beyond a filter 202. In FIG. 2B, a second catheter 212 having a magnetic distal end 222 is shown in position near the filter 202 within the vascular tissue 200, prior to engagement with the magnetic distal end 220 of the first catheter 210. In FIG. 2C, the first catheter 210 and second catheter 212 have been magnetically connected at their distal ends 220 and 222, forming a continuous channel through the respective catheters.

Figure 2D:
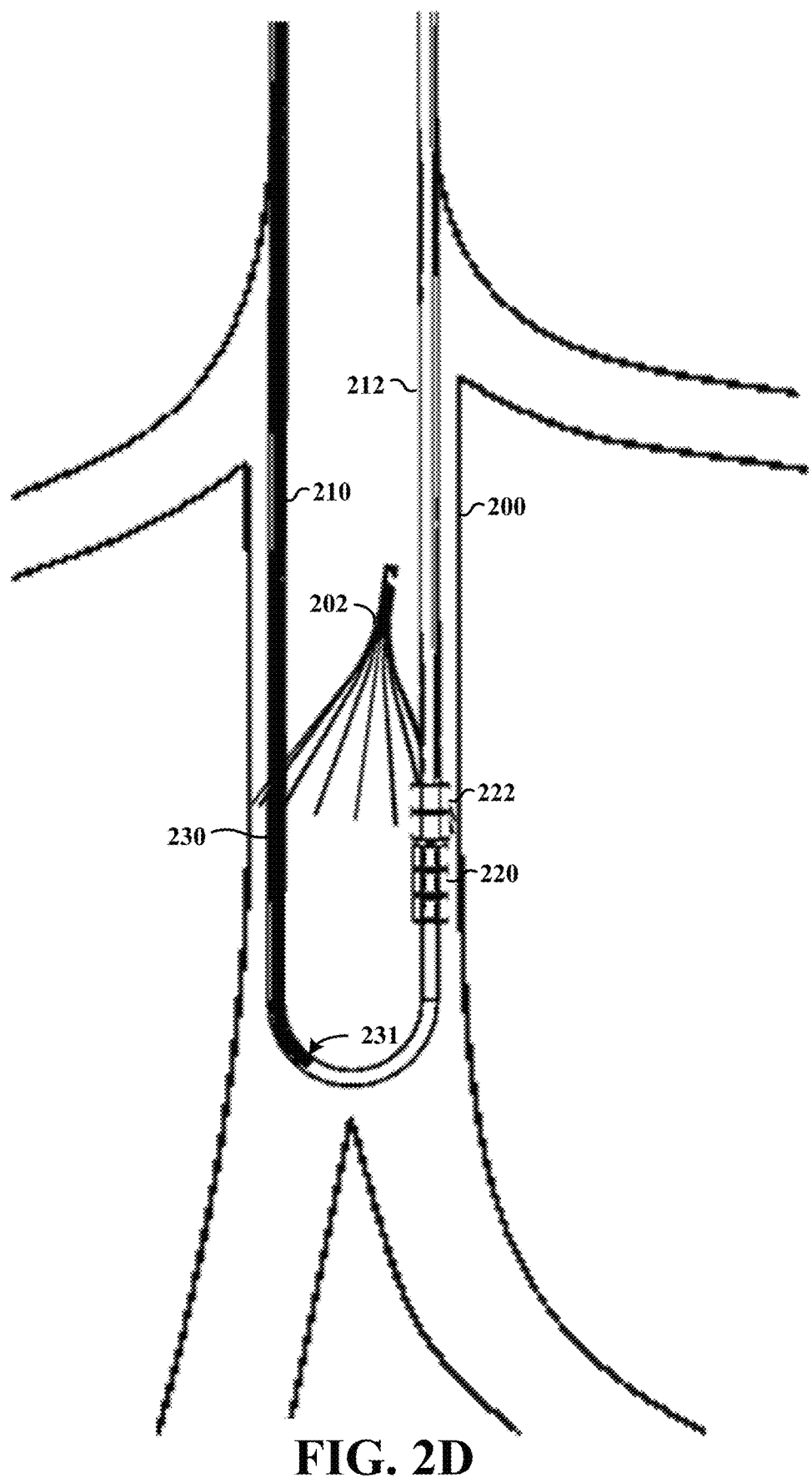
Figure 2E:
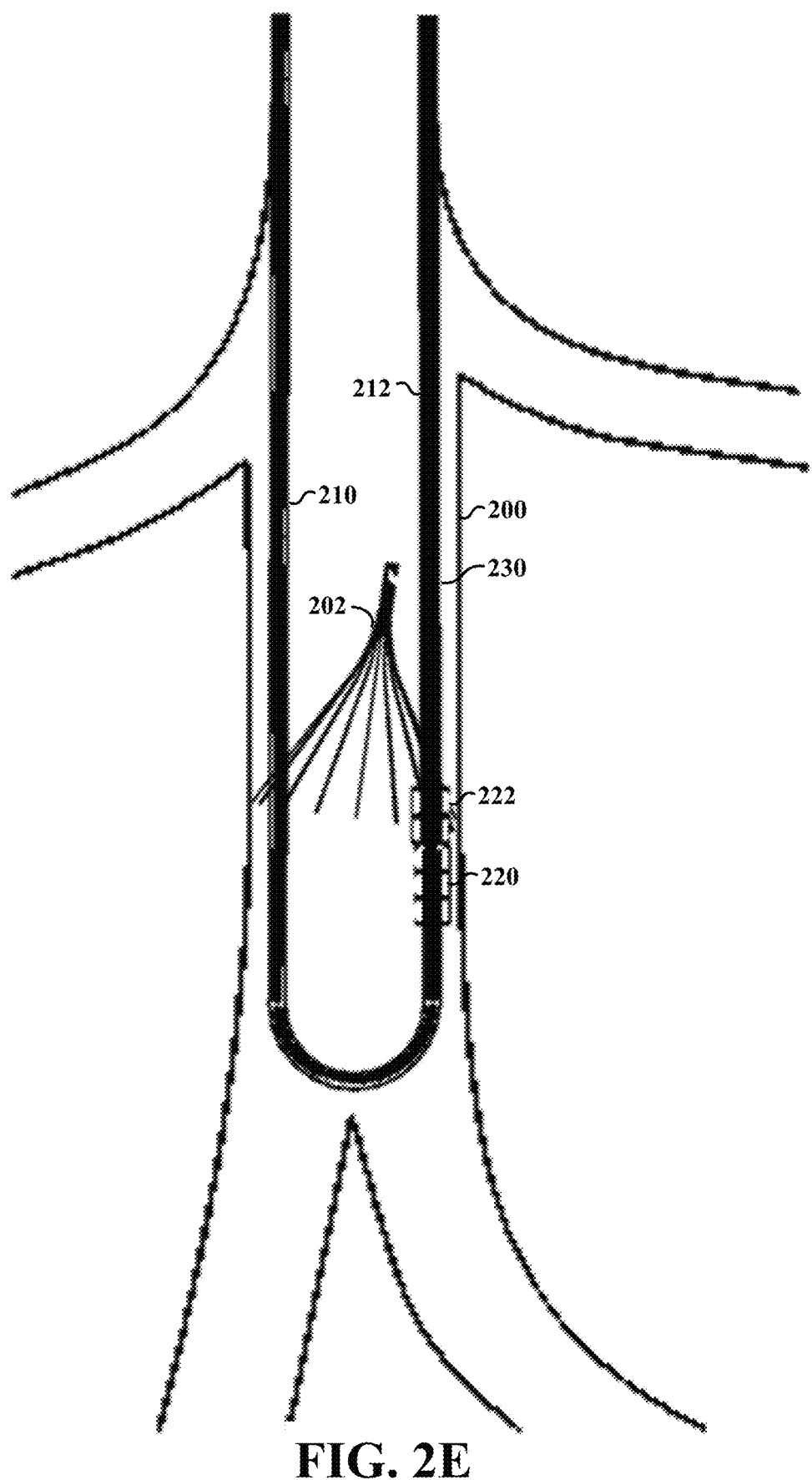
Figure 2F:
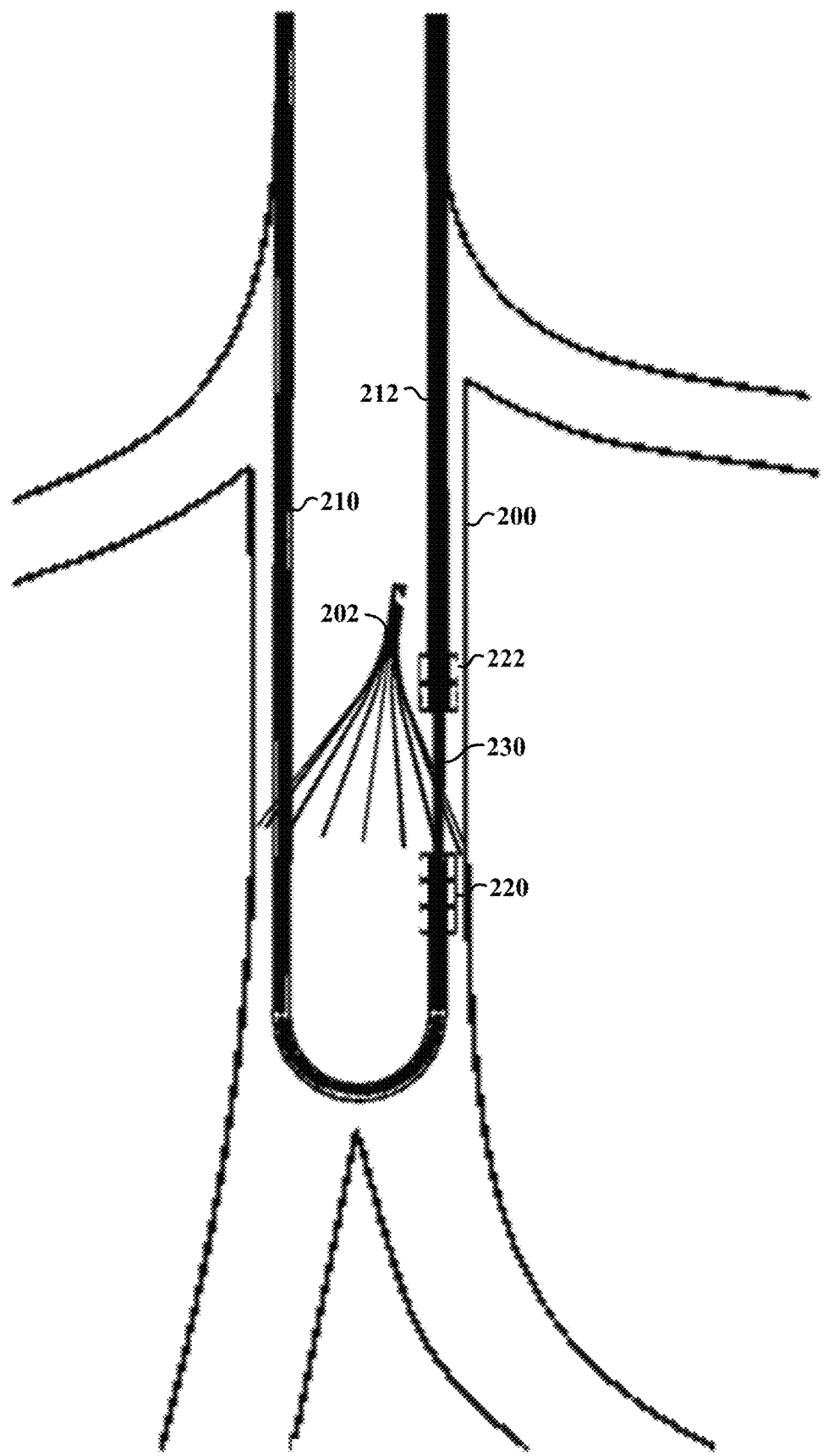

With the catheters joined, componentry can now be passed through the respective catheters. Referring to FIG. 2D, a wire 230 having an end 231 is shown partially inserted into catheter 210, extending partially around the bend as shown therein. In FIG. 2E, the wire 230 has been passed through the distal end 220 of the first catheter 210, into the distal end 222 of the second catheter 212, and further through at least a portion of the second catheter (e.g., the wire may be extend to a proximal end of the second catheter, external to the vascular tissue 200).

Figure 2G:
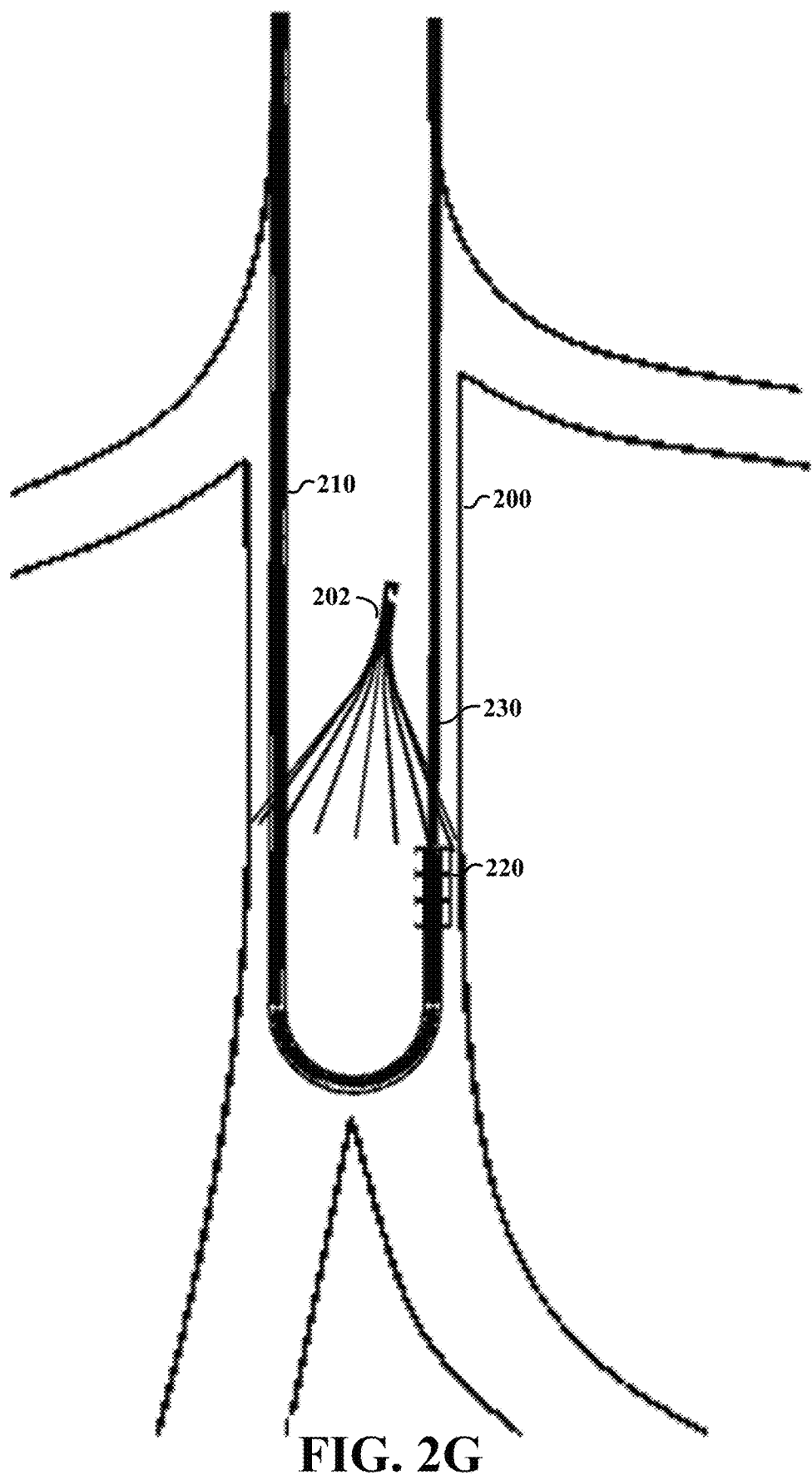
Figure 2H:
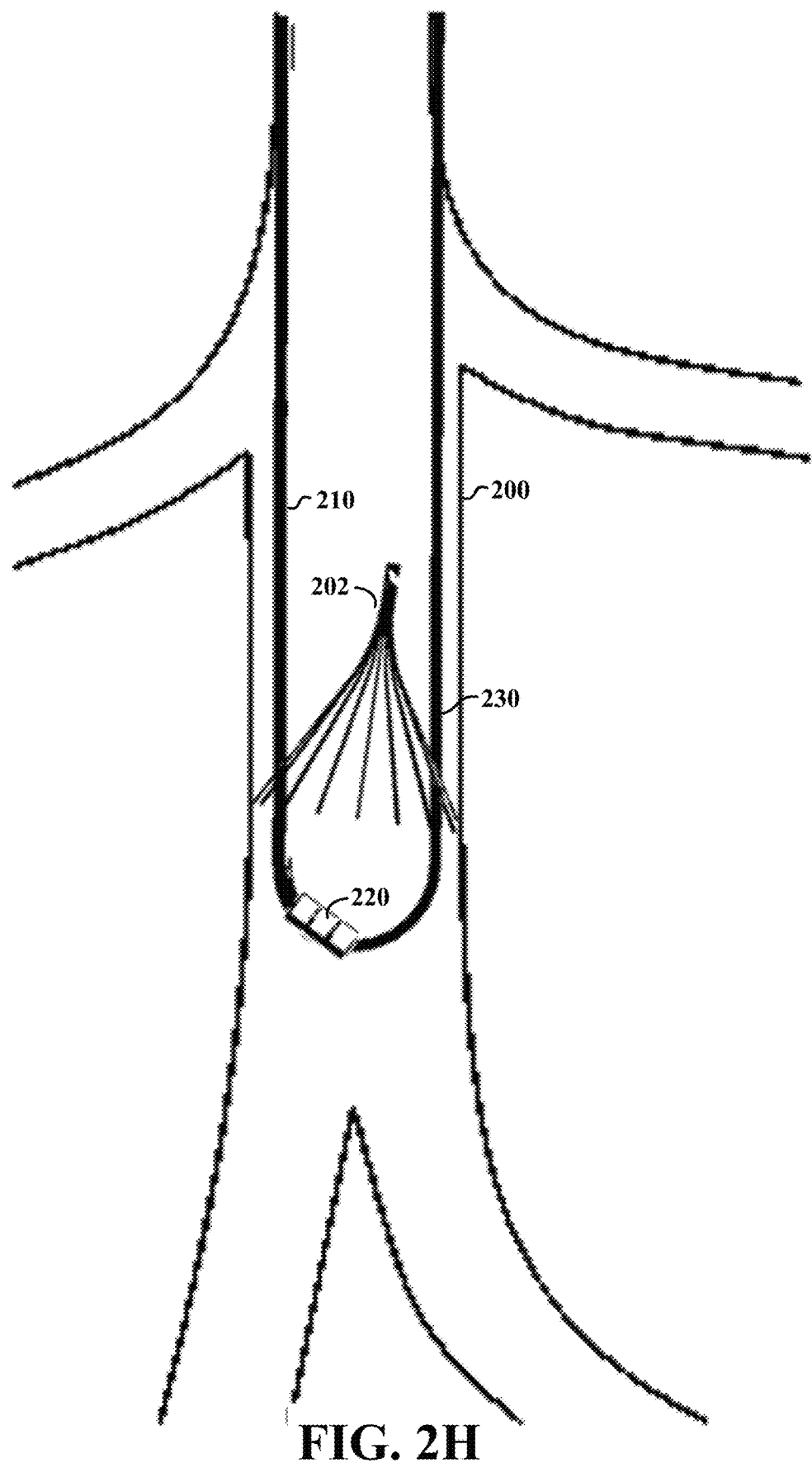

With the wire 230 in place, looped around the filter 202, the catheters can be removed. At FIG. 2F, the catheters 210 and 212 have been disconnected at their distal ends, with each respective catheter shown as partially retracted along the wire 230, a portion of which is exposed. In FIG. 2G, the catheter 212 has been retracted from view, for example, such as into a sheath as shown in FIG. 1A, or by removing the catheter from the vascular tissue (and/or completely from a patient). Catheter 210 is shown partially retracted in FIG. 2H, with the distal end 220 thereof passing around a bend in the wire 230.

Figure 2I:
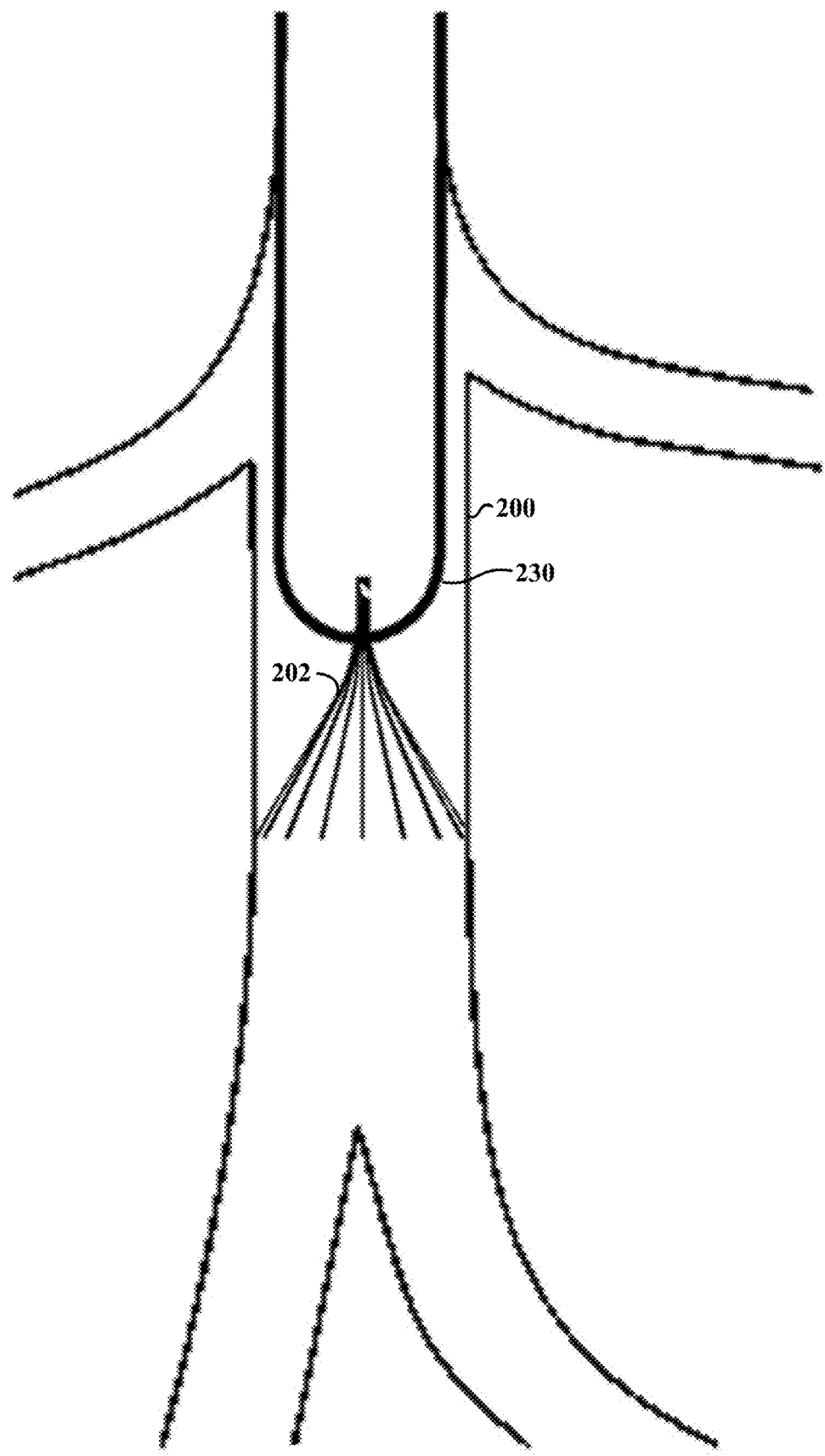
Figure 2J:
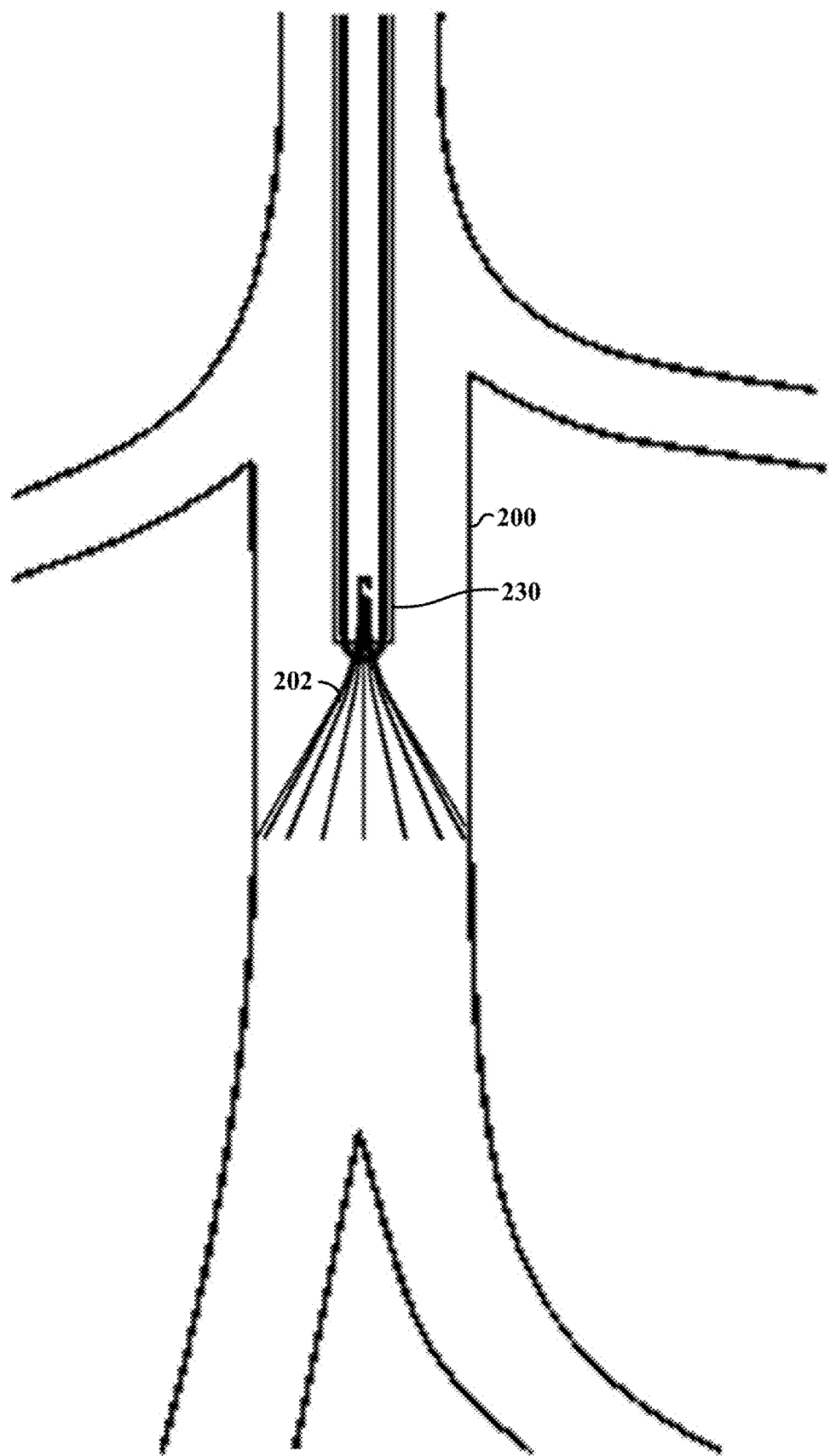

In FIG. 2I, both catheters have been completely removed from view (e.g., with catheter 210 also retracted into a sheath and/or removed from the vascular tissue 200), exposing the wire 230. The wire 230 has also been positioned with its loop around a base of the filter 202. In FIG. 2J, the wire 230 has been tightened around the filter 202, which is ready for extraction from the vascular tissue. Applying further tension to the wire (in the vertical direction as shown in the figure) effects removal of the filter 202. In various embodiments, one or more additional wires are deployed in a similar manner, prior to removal of the filter 202.

Figure 3:
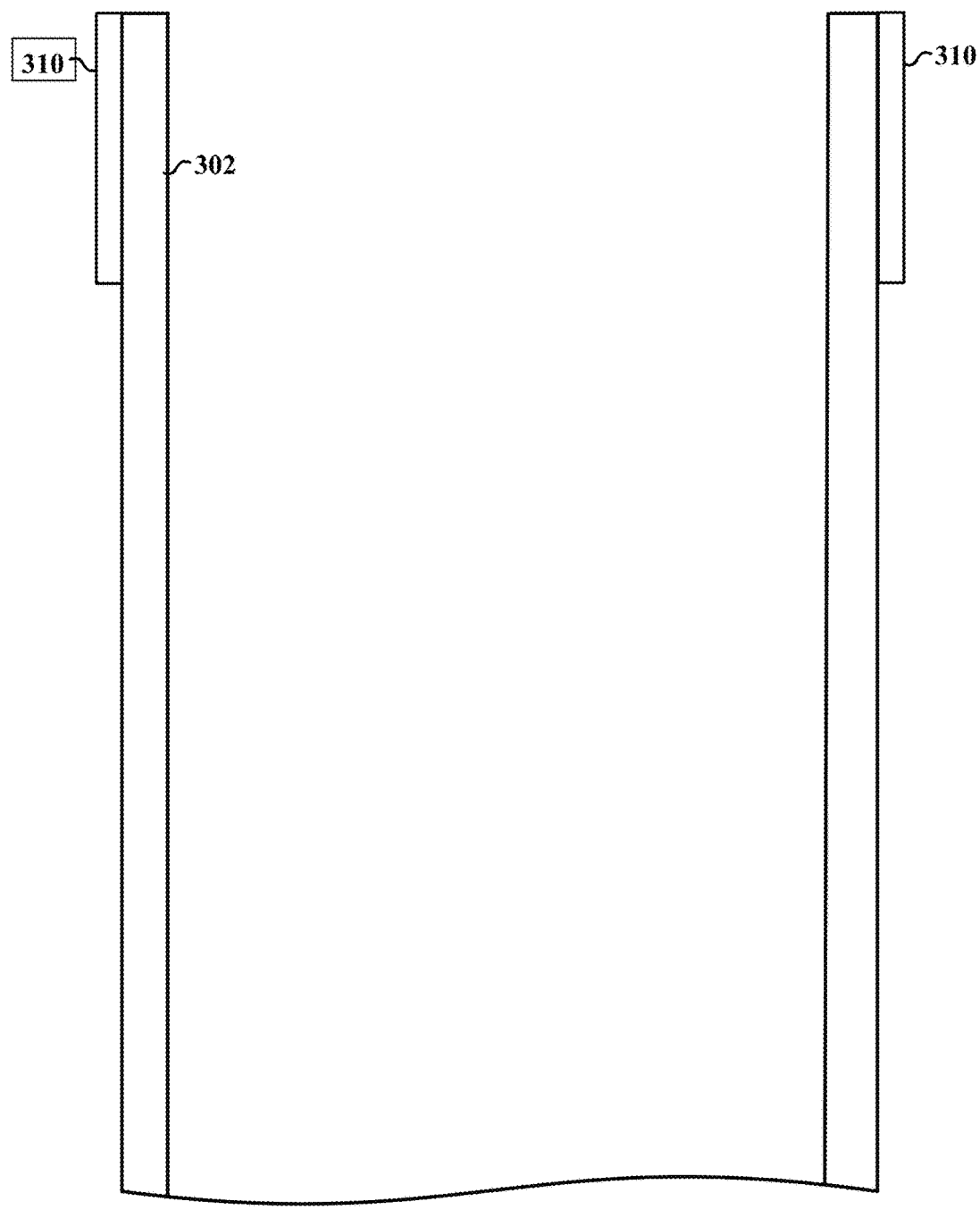
FIG. 3 shows a cross-sectional view of a distal end of a catheter having magnets on an outer wall of the catheter, as may be implemented in accordance with one or more embodiments.

FIG. 3 shows a cross-sectional view of a distal end of a catheter 300 having magnets on an outer wall of the catheter, as may be implemented in accordance with one or more embodiments. Magnet 310 is shown on an outer side of catheter wall 302.

Figure 4:
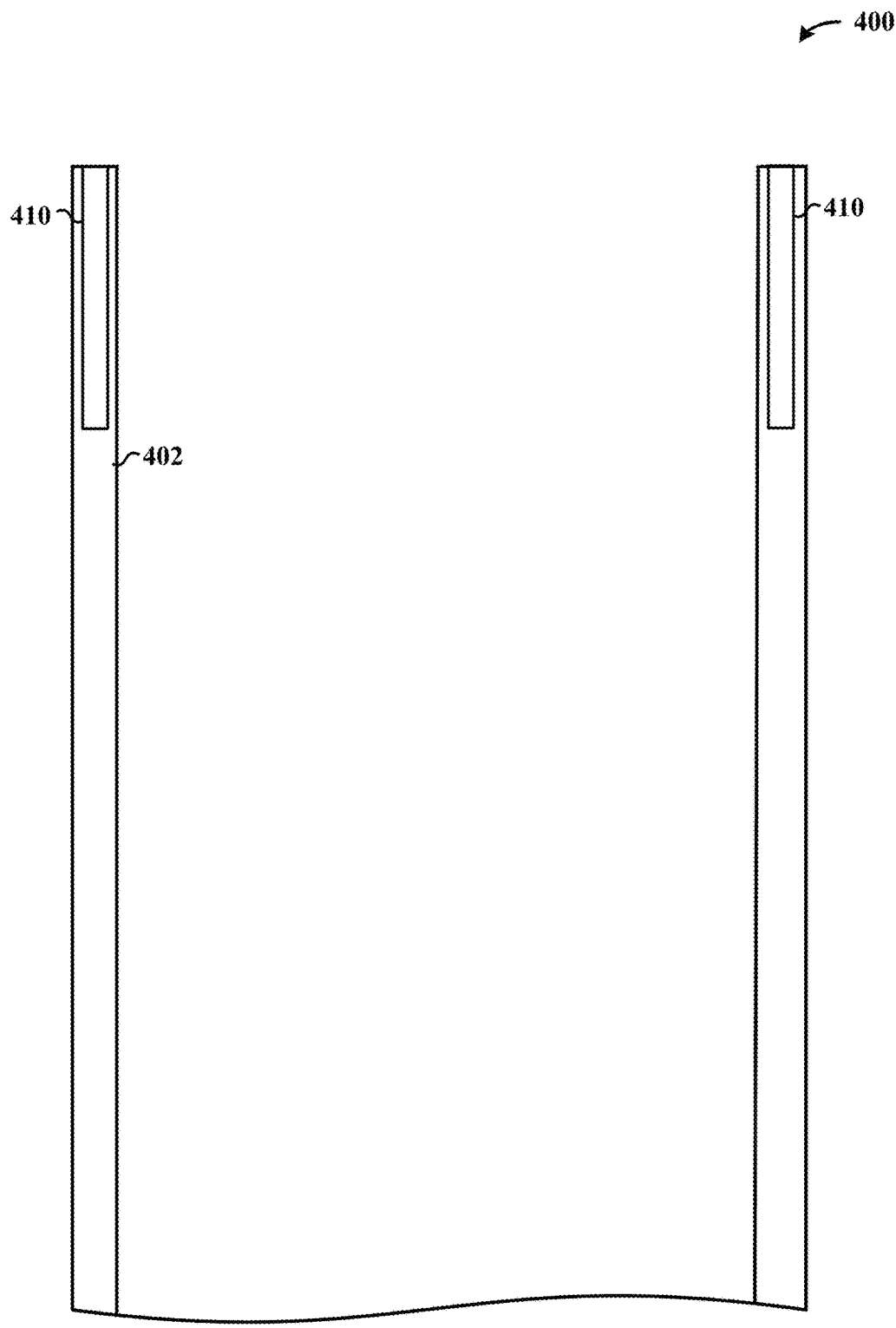
FIG. 4 shows a cross-sectional view of a distal end of a catheter having magnets integrated within a sidewall of the catheter, as may be implemented in accordance with one or more embodiments.

FIG. 4 shows a cross-sectional view of a distal end of a catheter 400 having magnets integrated within a sidewall of the catheter, as may be implemented in accordance with one or more embodiments. Magnet 410 is shown integrated within catheter wall 402.

Figure 5:
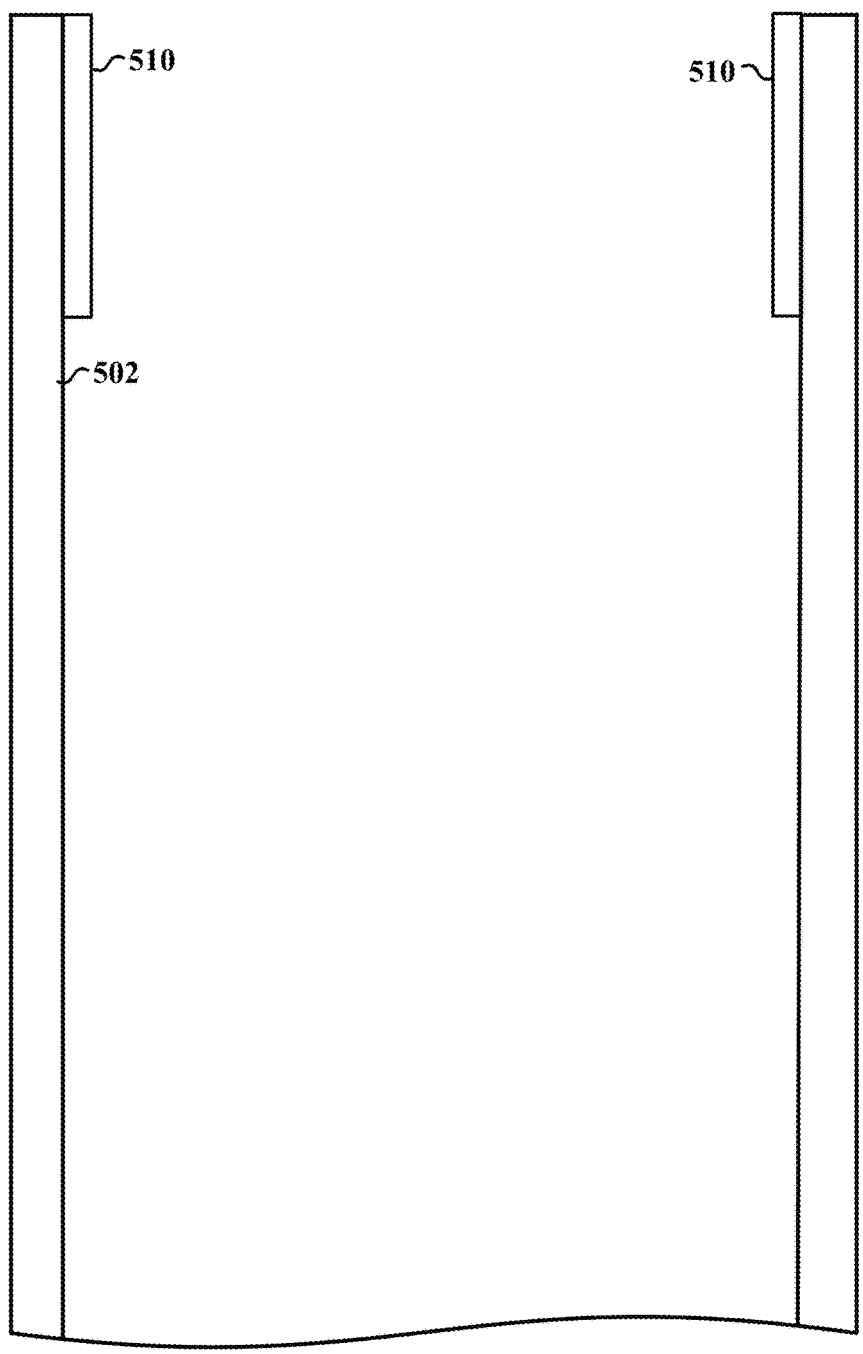
FIG. 5 shows a cross-sectional view of a distal end of a catheter having magnets on an inner wall of the catheter, as may be implemented in accordance with one or more embodiments.

FIG. 5 shows a cross-sectional view of a distal end of a catheter 500 having magnets on an inner wall of the catheter, as may be implemented in accordance with one or more embodiments. Magnet 510 is shown interfaced with an interior side of catheter wall 502.

As characterized herein, the apparatuses are applicable for use with a variety of approaches. FIGS. 6A-6F show respective steps in an approach for coupling respective portions of a catheter, as may be applicable (for example) for revascularization of an occlusion within an artery or vein. This approach can help address challenges to inserting a catheter or wire from one side until access through the occlusion is obtained. Catheter portions with magnetic ends can be inserted from different locations and joined (e.g., one from the neck and another from a vessel in the groin or behind the knee). Catheter portions can be placed in close enough proximity such that magnets on the end of each catheter couple, allowing a wire to be passed through to provide through-and-through access to the occlusion, which can then be treated (e.g., opened with balloons and fitted with a stent or stents).

Figure 6A:
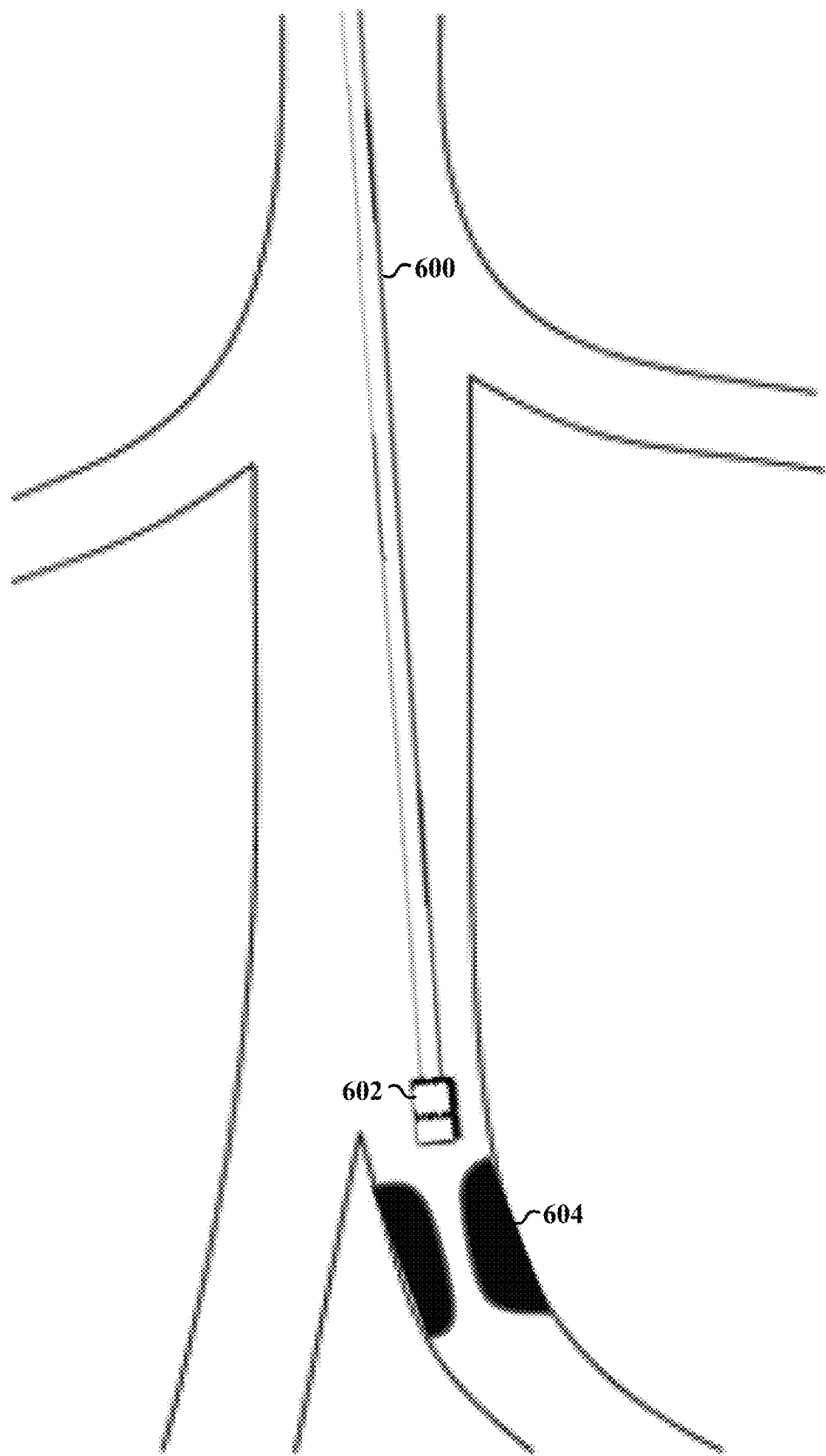
Figure 6B:
Figure 6C:
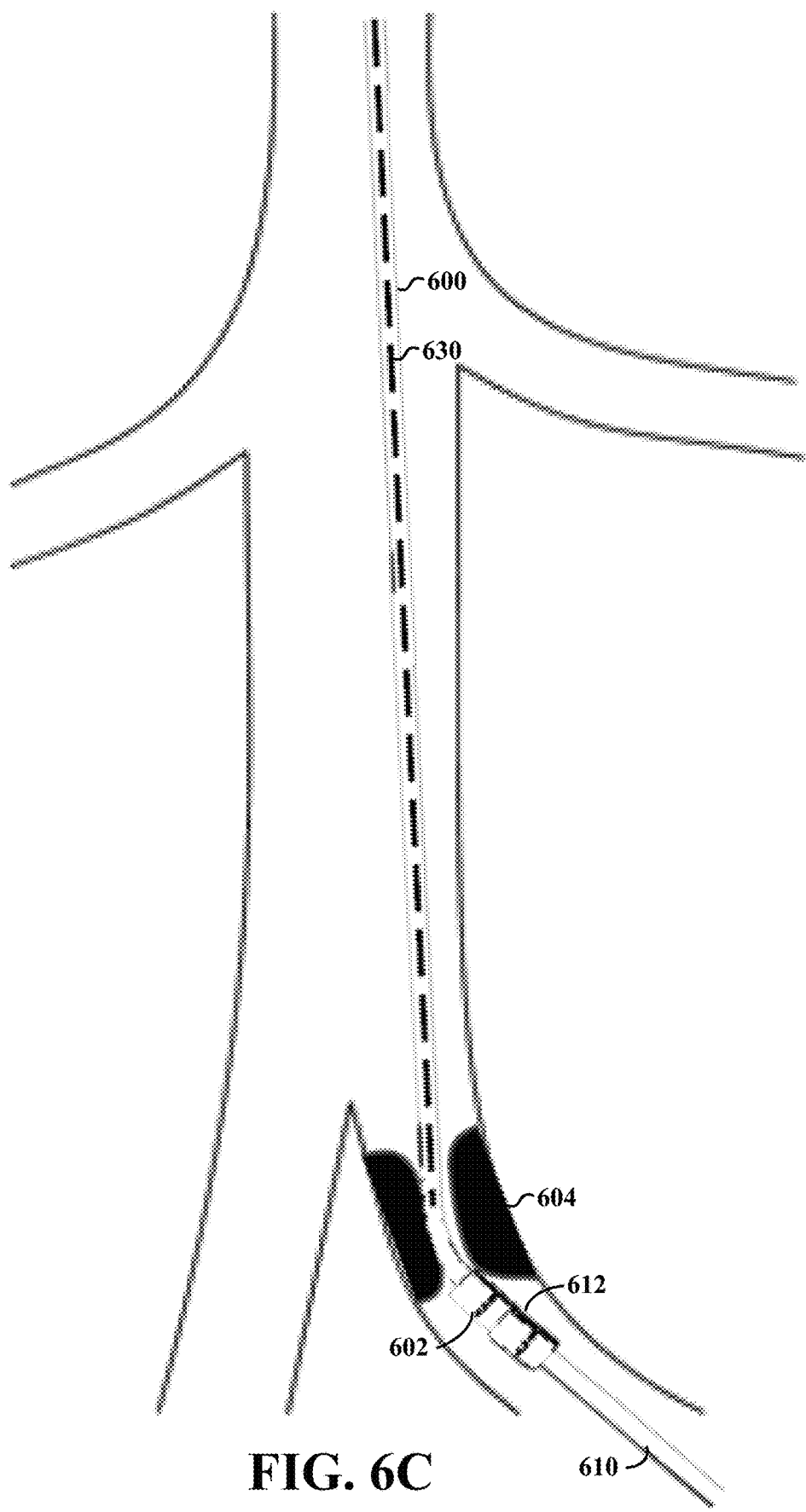
Figure 6D:
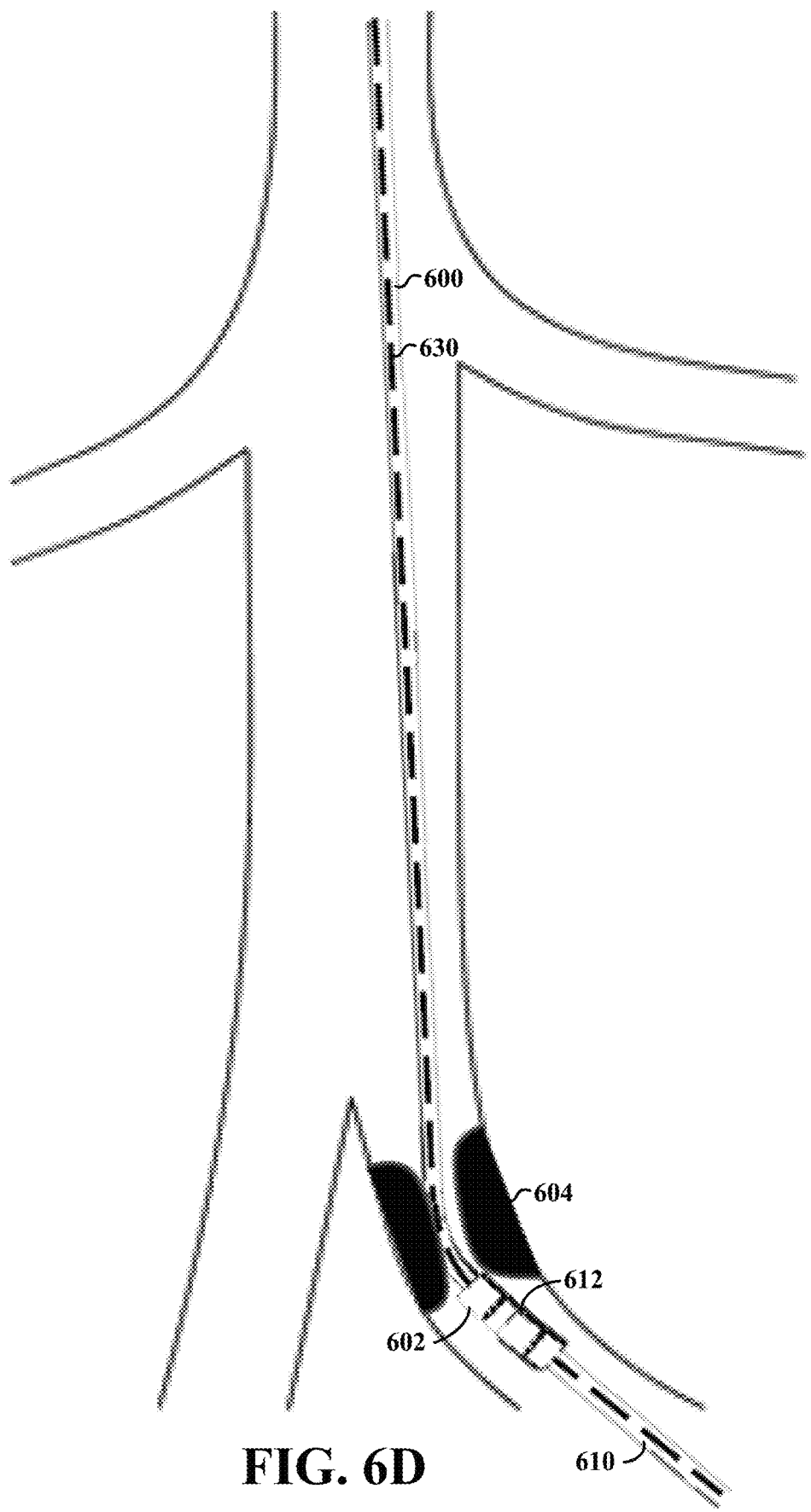
Figure 6E:
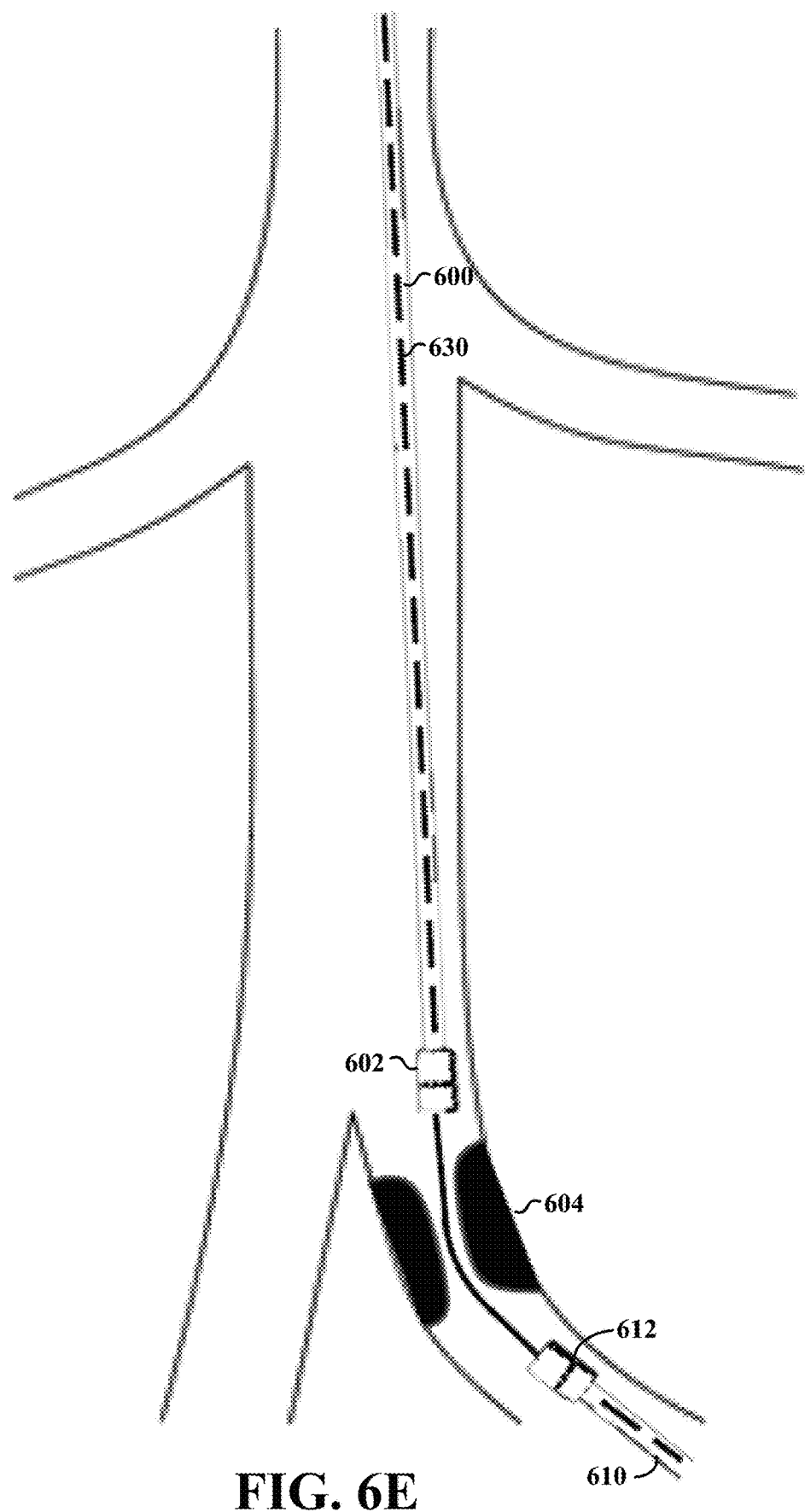
Figure 6F:
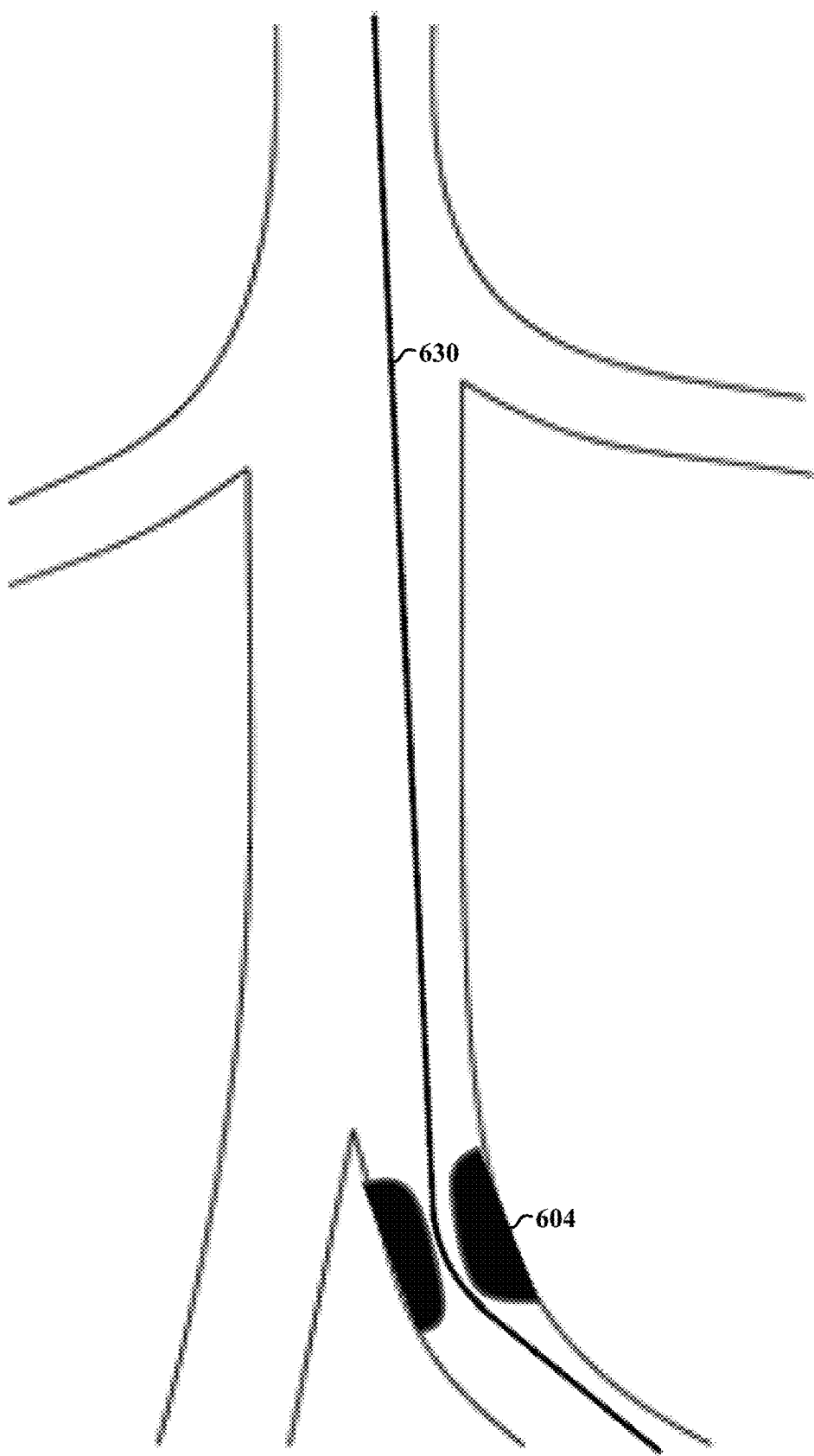

Beginning with FIG. 6A, a catheter 600 having a magnetic end 602 is inserted in an artery or vein (e.g., an internal jugular vein), and advanced therein to area having a severe occlusion or narrowing 604 (e.g., iliac vein). In FIG. 6B, a second catheter 610 having a magnetic end 612 is inserted into the artery or vein from an opposite direction (e.g., via the femoral vein), and advanced toward the occlusion 604 until the two magnets couple. A guide wire 630 is inserted into catheter 600 as shown in FIG. 6C, and advanced until it passes through the magnets 602 and 612, and through catheter 610 as shown in FIG. 6D. Once the guide wire 630 has been set in place, both catheters can be retracted as shown in FIG. 6E, and removed from the body as shown in FIG. 6F. With the catheters removed, the guide wire is left in place, creating a through-and-through access from one point of the body to another. This may provide, for example, access for a surgeon to open up the occlusion with balloons or stents.

Another application for a catheter or catheters as characterized herein may involve the insertion of a feeding tube, in accordance with FIGS. 7A-7F. For instance, a puncture may be made into a patient's stomach through the abdominal wall, and a first catheter may be passed into the stomach via the puncture. A second catheter may be passed into the stomach via the mouth and esophagus, joined with the first catheter and used to pass a wire extending through the mouth, esophagus, and out the abdominal wall. A feeding tube can then be advanced over the wire.

Figure 7A:
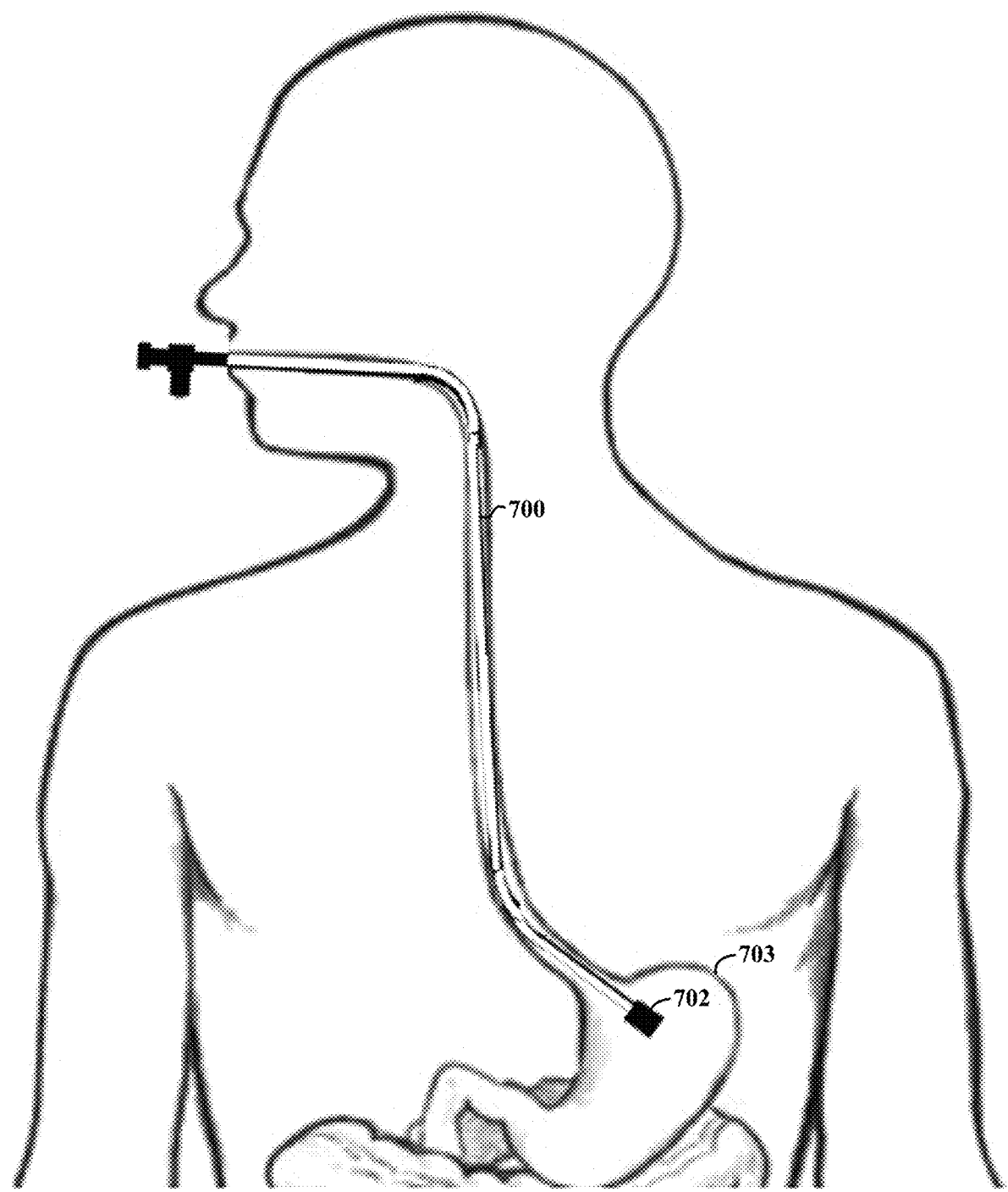
Figure 7B:
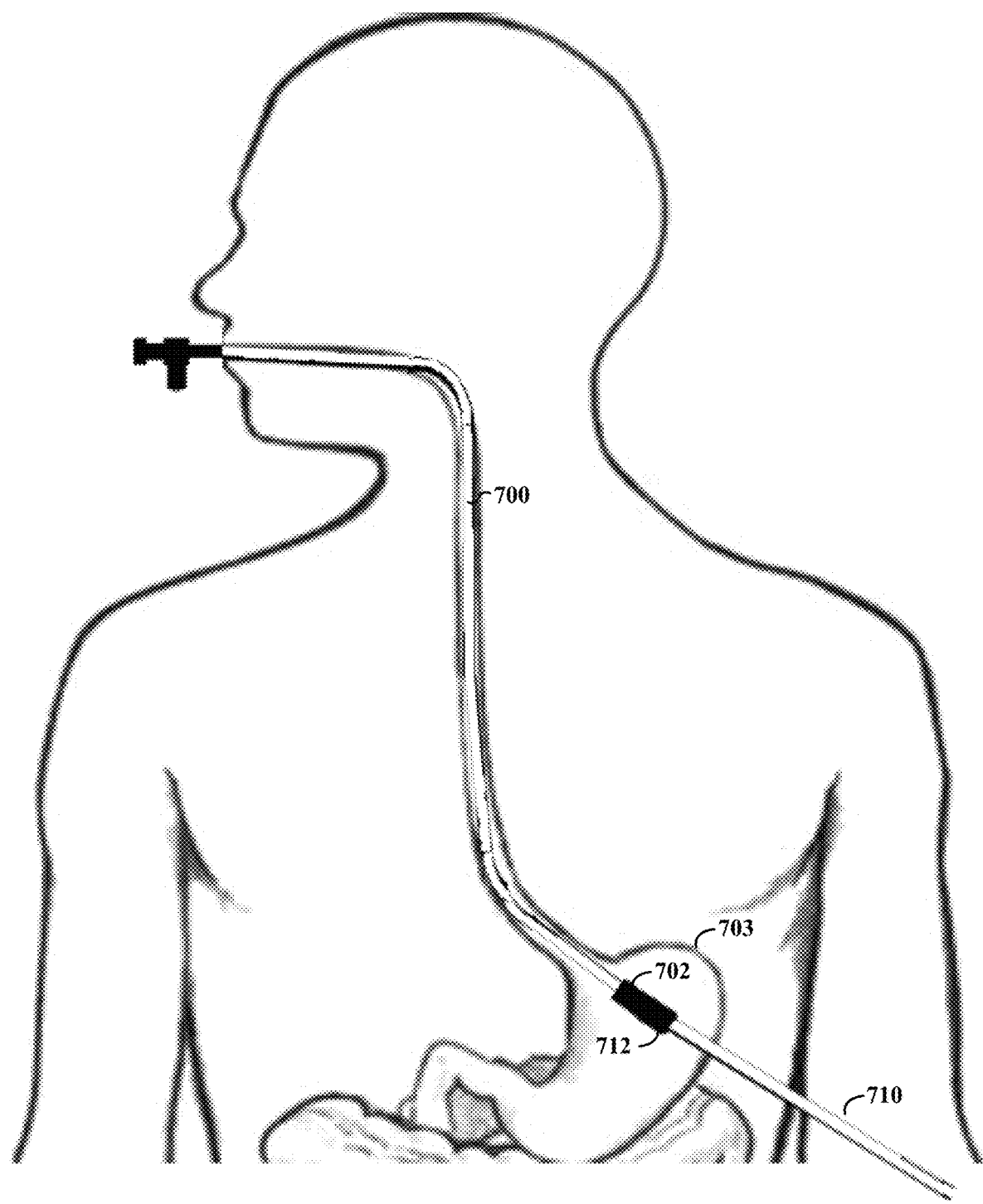
Figure 7C:
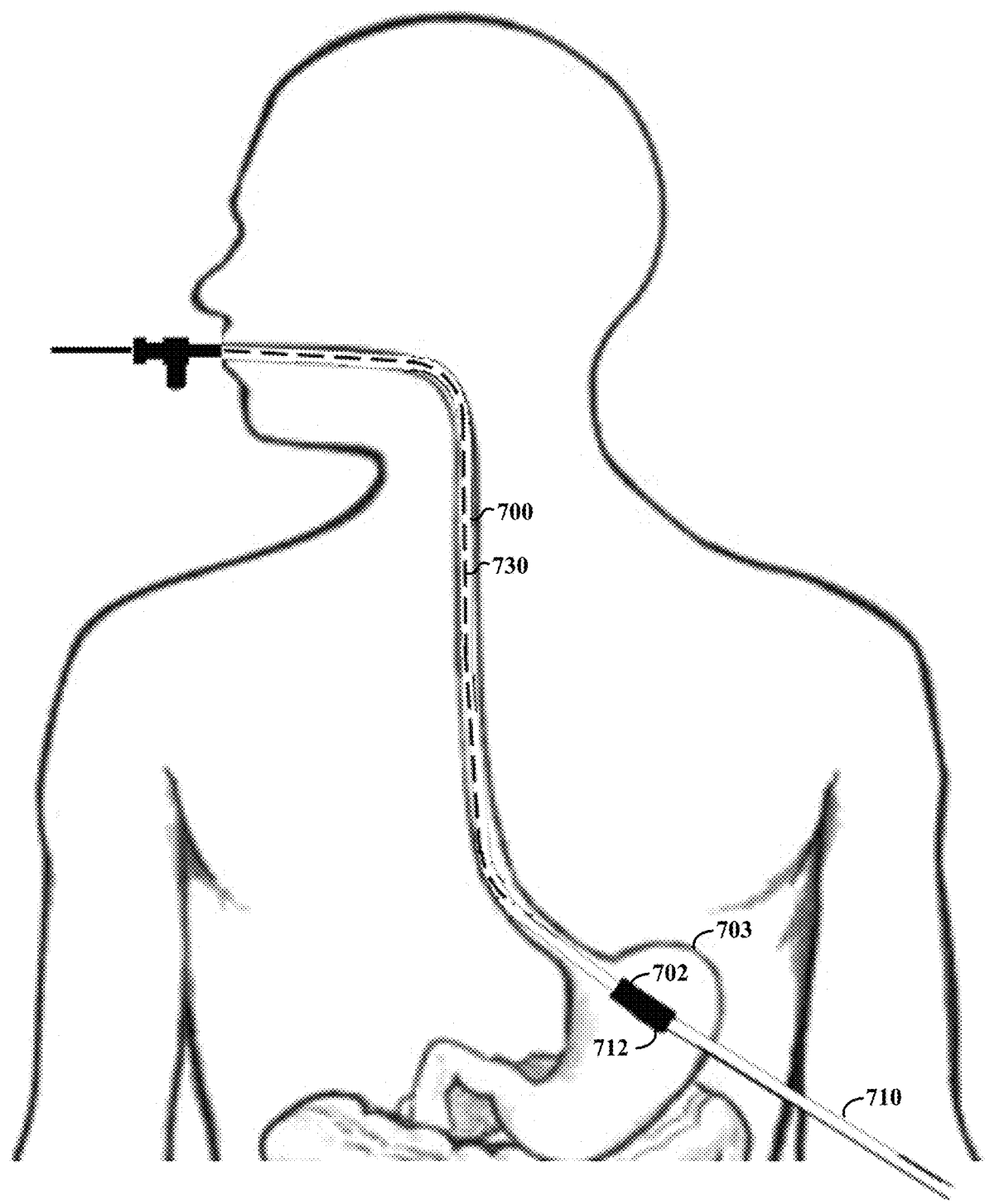
Figure 7D:
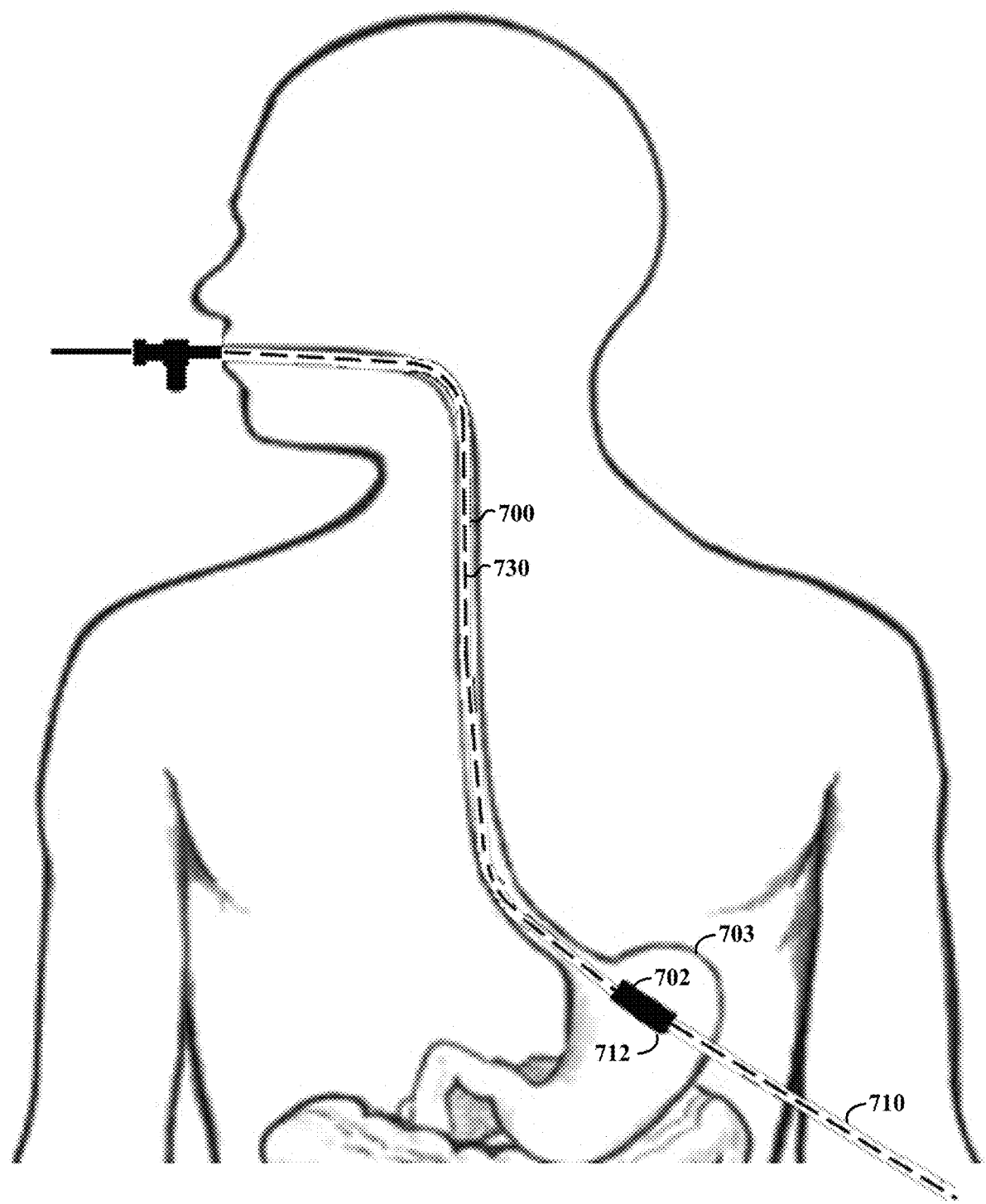
Figure 7E:
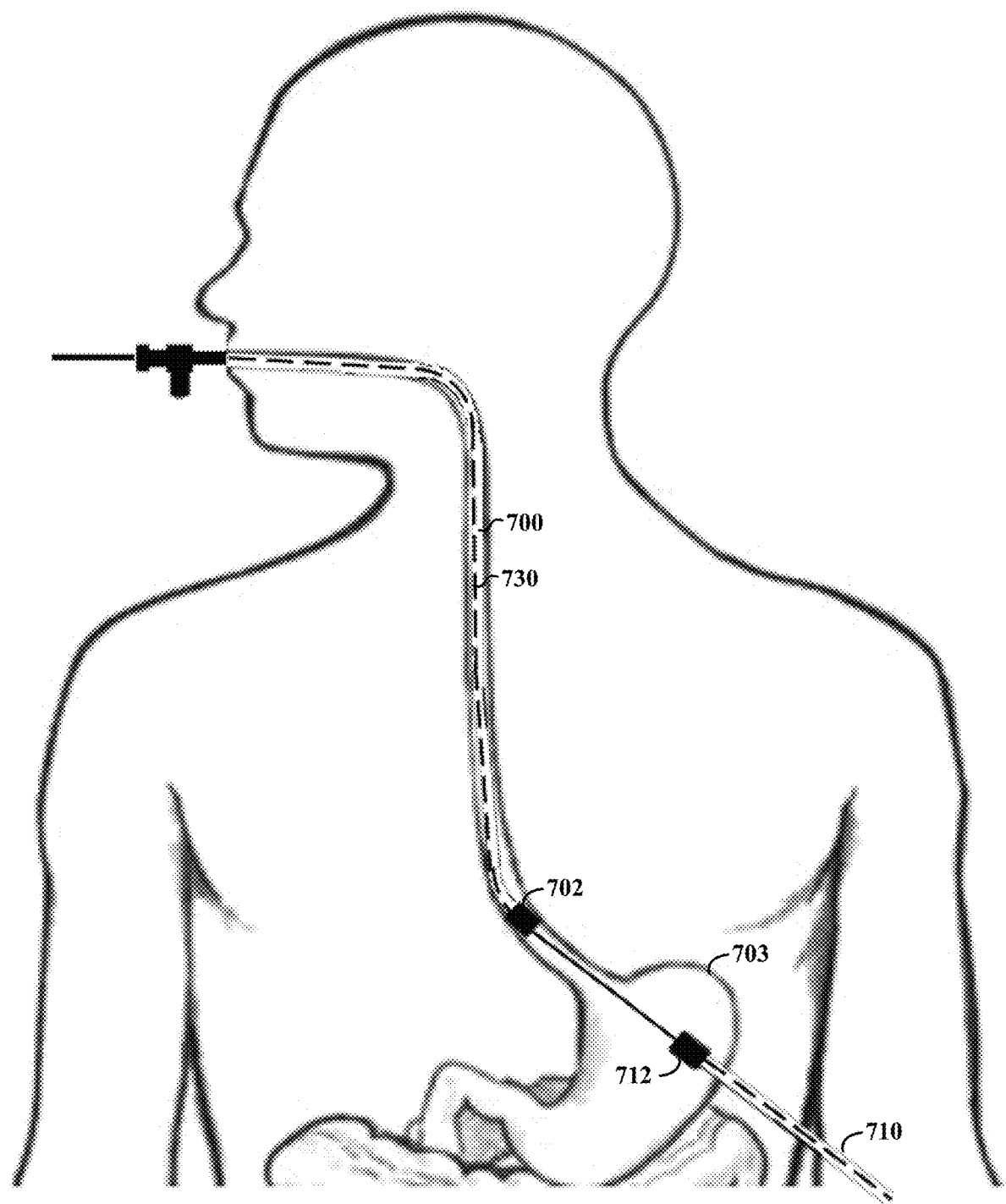
Figure 7F:
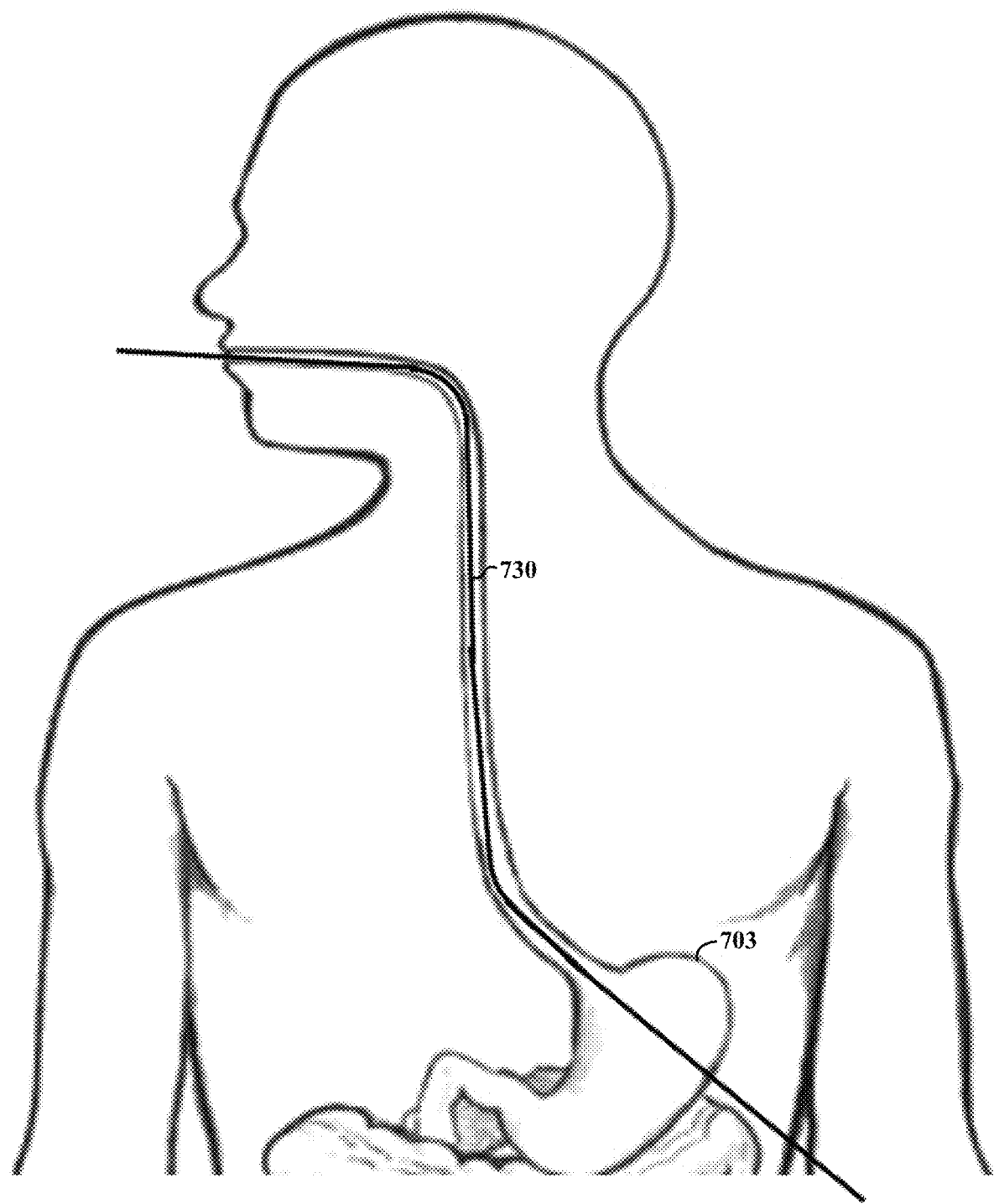

Referring to FIG. 7A, a catheter 700 having a magnetic end 702 is inserted into a patient's stomach 703 via the patient's mouth. In FIG. 7B, a second catheter 710 having a magnetic end 712 is inserted percutaneously into the stomach 703 via the abdominal wall. Continue to advance the catheter until the two magnets pair. A guide wire 730 is inserted through the catheter 700 in FIG. 7C, and advanced until it passes through the magnets 702/712 and out the other catheter 710 as shown in FIG. 7D. In FIG. 7E, retraction of both catheters is initiated, and the catheters are removed from the patient's body as shown in FIG. 7F, leaving the guide wire 730 in place and providing through-and-through access from the mouth, through the esophagus, and out the abdominal wall. A gastrostomy tube (e.g., feeding tube) can then be fed over the wire, through the mouth, and out the abdominal wall.

Figure 8:
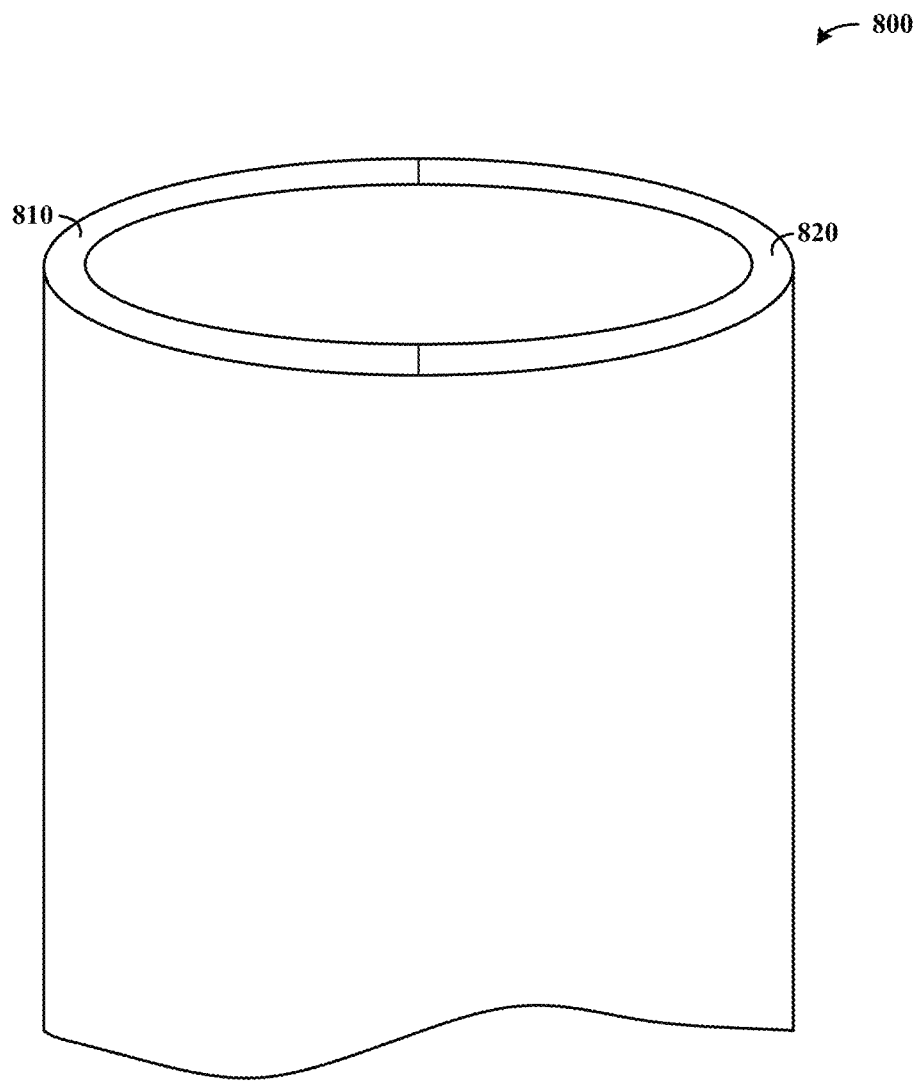
FIG. 8 shows a perspective view of a catheter having respective end portions with different magnetic properties, in accordance with another embodiment.

Referring to FIG. 8, a perspective view of a catheter 800 is shown having respective end portions 810 and 820 with different magnetic properties, in accordance with another embodiment. When two such catheters are brought into close proximity, they join magnetically in a manner as characterized herein. For removal, the catheters can be rotated relative to one another, such that the magnetic attraction between the catheters is diminished.

In some implementations, end portions 810 and 820 have magnetic poles that are opposite one another. These portions connect to another catheter having a similar end with opposing magnetic poles, such that the portions of each catheter having opposing poles relative to the other catheter magnetically attract one another. When the catheters are to be detached from one another, they may be rotated relative to each other so that end portions of each catheter having a common magnetic pole are brought into proximity with one another and repel each other for detachment.

In other implementations, end portion 810 is magnetic and end portion 820 has no magnetic properties. When another such catheter also has respective end portions that are non-magnetic and magnetic (of an opposite pole relative to end portion 810), the magnetic portions of the catheters attract one another and join. When the catheters are rotated relative to one another such that the respective magnetic portions are facing non-magnetic portions, they may be more easily detached.

The catheter 800 may thus be utilized in connection with various embodiments herein, such as those shown with magnets 120 and 122 in FIGS. 1A and 1B, or with magnets 602 and 612 in FIG. 6B. Further, additional regions of differing magnetic properties may be used, such as by having four or more regions of alternating poles. In addition, a variety of magnetic positioning may be used, such as shown in FIGS. 3-5, with the magnets therein having two or more sections of different magnetic poles.

In certain implementations, one or more steerable catheters are used to set, adjust or modify curvature of the catheter. For instance, a distal curve of a catheter may be modified via a dial or other component at a proximal end of the catheter, or by passing a wire having certain curvature or varied curvature at different positions along the wire, to suit particular applications. One or more such approaches could be utilized with catheter 210 in FIG. 2A or catheter 600 shown in FIG. 6B, for generating the respective bends as shown. This approach may, for example, be particularly useful in tailoring the position of the catheters relative to anatomy or physical dimensions of a filter (e.g., 202 of FIG. 2A). Further, steerable aspects can be utilized to decouple magnets, such as by facilitating rotation of the catheters as characterized with FIG. 8 and discussed above, or by otherwise applying a decoupling force. For general information regarding catheters, and for specific information regarding steerable aspects as may be implemented in accordance with one or more embodiments herein, reference may be made to: the steerable catheter sold under the trademark DiRex, available from Boston Scientific of Marlborough, Mass.; to the steerable sheath sold under the trademark HeartSpan, available from Merit Medical of South Jordan, Utah; and to the steerable introducer sold under the trademark Agilis and available from Abbot Laboratories of Abbott Park, Ill. Further, for general information regarding catheter wires, and for specific information regarding a tip-deflecting wire as may be utilized with one or more embodiments herein, reference may be made to the Reuter tip-defecting wire guide available from Cook Medical of Bloomington, Ind.

Various embodiments may also be carried out in the context of those embodiments characterized in the underlying provisional patent application, to which benefit is claimed and which is fully incorporated herein by reference. For instance, one or more embodiments may involve the method-based approaches characterized therein, for deploying a snare or other tool for removing a filter or other component from within vascular tissue.

Based upon the above discussion and illustrations, those skilled in the art will readily recognize that various modifications and changes may be made to the various embodiments without strictly following the exemplary embodiments and applications illustrated and described herein. For example, magnetic components can be implemented in a variety of manners, using different types of magnets (e.g., different shapes, or electromagnets). Further, different approaches can be used for alignment of the respective catheters, which may assist and/or replace magnetic alignment (and coupling). In addition, the various embodiments described herein may be combined in certain embodiments, and various aspects of individual embodiments may be implemented as separate embodiments. For instance, certain embodiments are directed to an individual catheter with a magnetic end, which may align to a multitude of components such as a complementary catheter as noted herein, or medical devices having a magnetic connection (e.g., for coupling to and delivery of drugs, fluid or other componentry). Such modifications do not depart from the true spirit and scope of various aspects of the invention, including aspects set forth in the claims.

What is claimed is:

1. An apparatus comprising: a first catheter extending from a proximal end to a distal end, the distal end having a magnet; a second catheter extending from a proximal end to a distal end, the distal end having a magnet, the second catheter being configured and arranged with the first catheter to align and directly connect the distal ends of the respective catheters via magnetic coupling of the magnets to one another; and a shaft structure configured and arranged with the first catheter and the second catheter to, with the first catheter aligned to and connected to the second catheter via the magnetic coupling, extend within the first catheter and into the second catheter, through the directly connected distal ends of the respective catheters.

2. The apparatus of claim 1, wherein the first catheter and the second catheter are configured and arranged to, with the shaft structure extending from the first catheter into the second catheter through the distal ends of the respective catheters, disconnect at the magnets and retract along the shaft structure to expose the shaft structure.

3. The apparatus of claim 1, wherein the first catheter and the second catheter are configured and arranged to disconnect from one another at the magnets and, with the shaft structure extending from the proximal end of the first catheter to the proximal end of the second catheter through the distal ends of the respective catheters, retract along the shaft structure to expose the shaft structure.

4. The apparatus of claim 1, wherein the first catheter has a bend that faces the distal end of the first catheter toward the proximal end of the first catheter.

5. The apparatus of claim 1, wherein:
the first catheter has a bend that directs the distal end of the first catheter back toward the proximal end of the first catheter with the bend extending further than the distal end, relative to the proximal end; and
the shaft is configured and arranged to flexibly extend within the bend of the first catheter as the shaft is extended through the first catheter and into the second catheter via the distal ends of the respective catheters while the distal ends are magnetically connected, therein forming a loop.

6. The apparatus of claim 1, wherein the respective magnets of the catheters are axially aligned with poles relative to the respective distal ends, and are configured and arranged to magnetically couple to one another with respective surfaces of the distal ends of the catheters in contact with one another and with the magnets axially aligned to one another.

7. The apparatus of claim 1, wherein the distal end of the first catheter has a surface that mates flush with a surface of the distal end of the second catheter when the respective distal ends are magnetically coupled to one another.

8. The apparatus of claim 1, wherein:
the first and second catheters are configured and arranged to extend around a graspable feature of a medical device located within vascular tissue in which the catheters are deployed, and to form a loop around the graspable feature upon connection of the distal ends via the magnetic coupling;
the shaft structure is configured and arranged to extend through the respective catheters and the distal ends thereof to loop around the graspable feature while the respective catheters are connected to one another;

the first and second catheters are configured and arranged to, with the shaft structure extended through the respective catheters and the distal ends thereof, disconnect at the magnets and retract along the shaft structure to expose the shaft structure in the vascular tissue; and the shaft structure is configured and arranged to, in response to a tension force applied in the direction of the proximal ends of the shaft, engage with and forcibly remove the medical device from its location within the vascular tissue.

9. The apparatus of claim 1, further including a sheath configured and arranged to house the first and second catheters, the first and second catheters being configured and arranged to extend from the sheath with each of the distal ends extending freely and separate from one another, prior to connection of the first catheter to the second catheter.

10. The apparatus of claim 1, wherein:

the magnet at the distal end of the first and second catheters each include different portions having opposite magnetic poles; and the first and second catheters are configured to disengage using magnetic repulsion in response to rotation of the first and second catheters relative to one another that aligns magnetic portions of a common magnetic pole in each of the first and second catheters with one another.

11. The apparatus of claim 1, wherein the second catheter is configured and arranged with the first catheter to connect the distal ends of the respective catheters by physically contacting surfaces of the distal ends to one another with the catheters extending away from one another and aligned with each other along a common direction.

12. A method comprising: deploying a first catheter extending from a proximal end to a distal end, the distal end having a magnet; deploying a second catheter extending from a proximal end to a distal end, the distal end having a magnet; aligning and directly connecting the distal ends of the respective catheters via magnetic coupling of the magnets to one another; and with the first catheter aligned to and directly connected to the second catheter via the magnetic coupling, extending a shaft structure within the first catheter and into the second catheter, through the directly connected distal ends of the respective catheters.

13. The method of claim 12, further including:

disconnecting the distal ends of the first catheter and the second catheter from one another, with the shaft structure extending from the first catheter into the second catheter through the distal ends of the respective catheters, and retracting the first catheter and the second catheter along the shaft structure to expose the shaft structure.

14. The method of claim 12, further including:

disconnecting the distal ends of the first catheter and the second catheter from one another, with the shaft structure extending from the proximal end of the first catheter to the proximal end of the second catheter through the distal ends of the respective catheters; and retract the first catheter and the second catheter along the shaft structure to expose the shaft structure.

15. The method of claim 12, wherein deploying the first catheter includes deploying a bend at the distal end of the first catheter facing back toward the proximal end of the first catheter.

16. The method of claim 12, wherein:

deploying the first catheter includes deploying a bend near the distal end of the first catheter facing back toward the proximal end of the first catheter with the bend extending further than the distal end, relative to the proximal end; and extending the shaft structure includes flexibly extending the shaft structure through the bend of the first catheter back toward the proximal end of the first catheter, and into the second catheter via the distal ends of the respective catheters while the distal ends are magnetically connected, therein forming a loop.

17. The method of claim 12, wherein:

the respective magnets of the catheters are axially aligned with poles relative to the respective distal ends and the catheters, and aligning and connecting the distal ends of the respective catheters includes magnetically coupling the magnets to one another with respective surfaces of the distal ends of the catheters in contact with one another and with the magnets axially aligned to one another.

18. The method of claim 12, wherein aligning and connecting the distal ends of the respective catheters includes mating an end surface of the distal end of the first catheter flush with an end surface of the distal end of the second catheter, with the distal ends magnetically coupled to one another.

19. The method of claim 12, wherein:

deploying the first catheter and deploying the second catheter includes positioning the respective catheters to form a loop around a graspable feature of a medical device located within vascular tissue in which the catheters are deployed; and extending the shaft structure by extending the shaft structure through the respective catheters and the distal ends thereof to loop around the graspable feature while the respective catheters are connected to one another.

20. The method of claim 19, further including disconnecting the respective catheters at the distal ends thereof, and retracting the catheters along the shaft structure to expose the shaft structure in the vascular tissue.

21. The method of claim 20, further including:

applying a tension force to the shaft structure in the direction of the proximal ends of the shaft; and engaging with and forcibly removing the medical device from its location within the vascular tissue.

22. A method for removing a filter from vascular tissue, the method comprising:

deploying a first catheter into the vascular tissue, the first catheter extending from a proximal end to a distal end, the distal end having a J-curve and a magnet axially aligned with the first catheter, with the J-curve extending partially around a structure of the filter;

deploying a second catheter in the vascular tissue, extending from a proximal end to a distal end, the distal end having a magnet axially aligned with the second catheter and having a magnetic pole that is arranged opposite the pole of the magnet of the first catheter;

aligning and connecting the distal ends of the respective catheters via magnetic coupling of the magnets to one another, therein forming a continuous channel through the respective catheters in a loop around the structure of the filter;

with the first catheter aligned to and connected to the second catheter via the magnetic coupling and extending in the loop, extending a wire within the first catheter and into the second catheter, through the connected distal ends of the respective catheters, the wire forming a loop around the structure of the filter;

retracting the first and second catheters along the wire, exposing the wire in the vascular tissue; and removing the filter by pulling on the wire, using the looped portion thereof to grasp and dislodge the filter from the vascular tissue.

\* \* \* \* \*